(12) United States Patent
Phillips et al.

(10) Patent No.: US 6,416,991 B1
(45) Date of Patent: Jul. 9, 2002

(54) HUMAN CYCLIC NUCLEOTIDE PDES

(75) Inventors: Stephen C. Phillips, Canterbury; Jerry Lanfear, Ashford; Lindsay Fawcett, Canterbury, all of (GB); Olga Bandman, Mountain View, CA (US); Ian Harrow, Herne Bay (GB)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/595,514

(22) Filed: Jun. 14, 2000

Related U.S. Application Data

(63) Continuation-in-part of application No. 09/226,741, filed on Jan. 7, 1999, now Pat. No. 6,100,037.

(51) Int. Cl.[7] .......................... C12N 9/16; C07K 16/40
(52) U.S. Cl. .................. 435/196; 435/19; 530/387.9
(58) Field of Search ............................. 435/196, 6, 7, 435/1, 19; 530/387.9

(56) References Cited

PUBLICATIONS

Mennella, M.R.F., et al. (1076) Andrologia 9(1), 15–22.*
Beavo, J.A., Cylic Nucleotide Phosphodiesterases: Functional Implications of Multiple Isoforms, Physiological Reviews, 75(4) : 725–48, (Oct. 1995).
McAllister–Lucas, L.M. et al., The Structure of a Bovine Lung cGMP–binding, cGMP–specific Phosphodiesterase Deduced from a cDNA Clone, J. Biol. Chem. 268(38) :22873, (1993).
Turko, I.V. et al., Identification of Key Amino Acids in a Conserved cGMP–binding Site of cGMP–binding Phosphodiesterases, J. Biol. Chem. 271(36) :22240–22244, (1996).
Verghese et al., Mol. Pharmacol. 47: 1164–1171 (1995).
Angel, Rolipram, a specific type IV phosphodiesterase inhibitor is a potent inhibitor of HIV–1 replication, J.B. et al., AIDS 9:1137–44, (1995).
Sommer, The antidepressant roligram suppresses cytokine production and prevents autoimmune enephalomyelitis, N. et al., Nat. Med. 1(3) :244–248, (1995).
Sasaki, H. et al., Suppression of oro–facial movements by roligram, a cAMP phosphodiesterase inhibitor, in rats chronically treated with haloperidol, Eur. J. Pharmacol 282:71–76, (1995).
Banner, K.H. and Page, Theophylline and selective phosphodiesterase inhibitors as anti–inflammatory drugs in the treatment of bronchial asthma, C.P., Eur. Respir. J. 8:996–1000, (1995).
Stacey, P. et al., (Direct Submission) NCBI Accession No. CAA6170 (GI 3355606), Jul. 24, 1998.
Hurwitz, R.L. et al., "Immunologic Characterization of the Photoreceptor Outer Segment Cyclic GMP Phosphodiesterase", J. Biol. Chem. 259: 8612–8618 (1984).

* cited by examiner

Primary Examiner—Charles L. Patterson, Jr.
(74) Attorney, Agent, or Firm—Incyte Genomics, Inc.; Lynn E. Murry

(57) ABSTRACT

The invention provides human cyclic nucleotide phosphodiesterases (HSPDE10A) and polynucleotides which identify and encode HSPDE10A. The invention also provides expression vectors, host cells, antibodies, agonists, and antagonists and methods for diagnosing or treating disorders associated with expression of HSPDE10A.

7 Claims, 22 Drawing Sheets

Figure 4A:
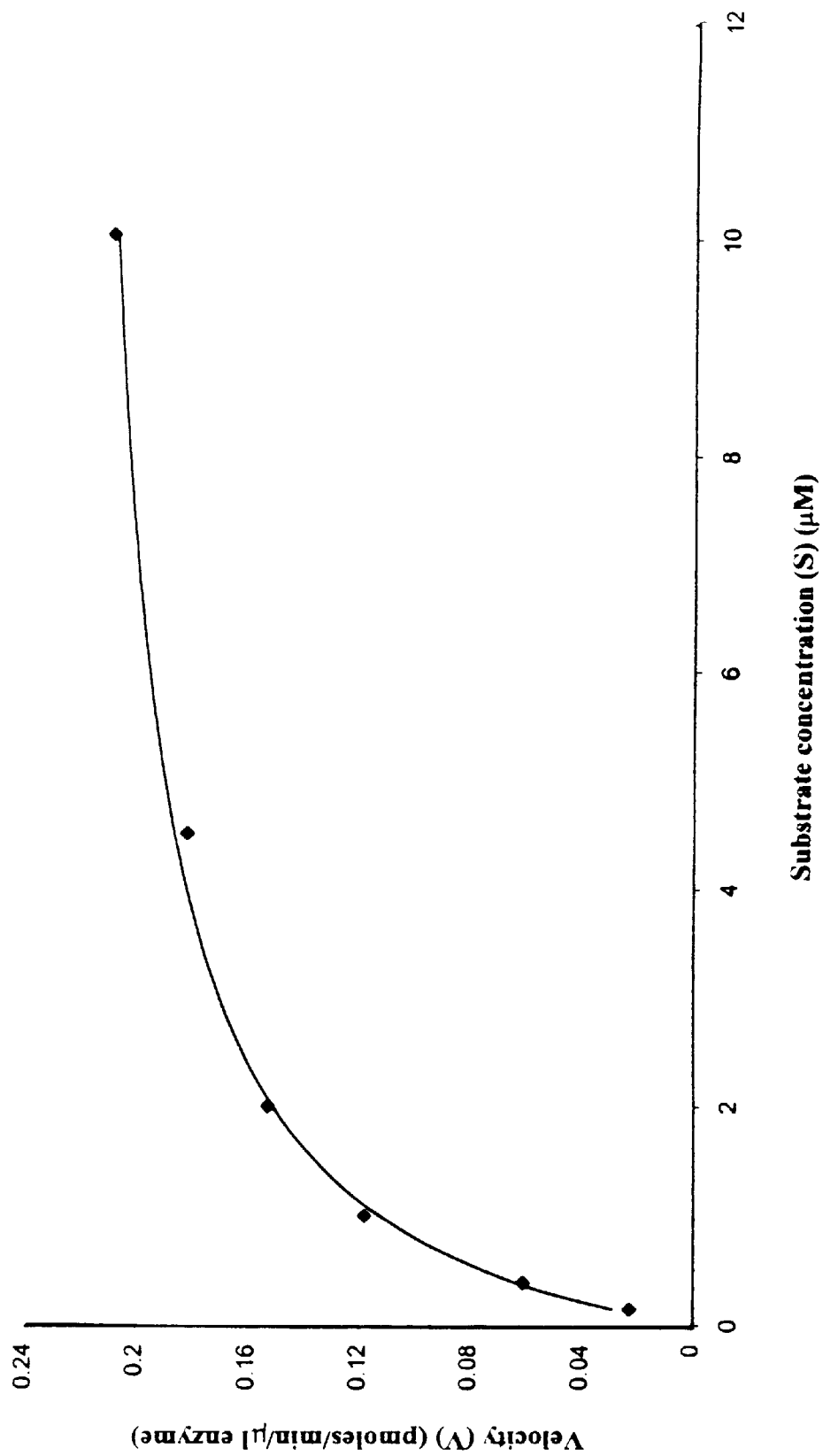

```
5' TGG AAA GAT GTT ACT TCA TCT CCC AGG TTT GCT CAC TGC AAA TAC AAT CCT GAG
      9          18          27          36          45          54

AAC TGA ACT AGG GCC TTA AAG TCC TGA CAT GCA TGG CTT GGT TTT GTG GAT TGC
         63          72          81          90          99         108

CTC TCT CAA CAG GTG AAA TTT ACC AAA TCC TTT GAA TTG ATG TCC CCA AAG
        117         126         135         144         153         162
                                                         M   S   P   K

TGC AGT GCT GAT GCT GAG AAC AGT TTC AAA GAA ATG AGC ATG GAG AAA TCA TCA TAC
        171         180         189         198         207         216
     C   S   A   D   A   E   N   S   F   K   E   S   M   E   K   S   S   Y

TCC GAC TGG CTA ATA AAT AAC AGC ATT GCT GAG CTG GTT GCT TCA ACA GGC CTT
        225         234         243         252         261         270
     S   D   W   L   I   N   N   S   I   A   E   L   V   A   S   T   G   L

CCA GTG AAC ATC AGT GAT GCC TAC CAG GAT CCG CGC TTT GAT GCA GAG GCA GAC
        279         288         297         306         315         324
     P   V   N   I   S   D   A   Y   Q   D   P   R   F   D   A   E   A   D

CAG ATA TCT GGT TTT CAC ATA AGA TCT GTT CTT TGT GTC CCT ATT TGG AAT AGC
        333         342         351         360         369         378
     Q   I   S   G   F   H   I   R   S   V   L   C   V   P   I   W   N   S
```

FIGURE 1A

```
       387         396   405         414         423         432
AAC CAC CAA ATA ATT GGA GTG GCT CAA GTG TTA AAC AGA CTT GAT GGG AAA CCT
 N   H   Q   I   I   G   V   A   Q   V   L   N   R   L   D   G   K   P 441         450   459         468         477         486
TTT GAT GAT GCA GAT CAA CGA CTT TTT GAG GCT TTT GTC ATC TTT TGT GGA CTT
 F   D   D   A   D   Q   R   L   F   E   A   F   V   I   F   C   G   L 495         504   513         522         531         540
GGC ATC AAC AAC ACA ATT ATG TAT GAT CAA GTG AAG TCC TGG GCC AAG CAG
 G   I   N   N   T   I   M   Y   D   Q   V   K   S   W   A   K   Q 549         558   567         576         585         594
TCT GTG GCT CTT GAT GTG CTA TCA TAC CAT GCA ACA TGT TCA GAA GCT GAA GTT
 S   V   A   L   D   V   L   S   Y   H   A   T   C   S   E   A   E   V 603         612   621         630         639         648
GAC AAG TTT GAT GAC AAG GCA GCC AAC ATC CCT CTG GTG TCA GAA CTT GCC ATG ATC GCC ATG GAT GAC
 D   K   F   D   D   K   A   A   N   I   P   L   V   S   E   L   A   M   I   D   D 657         666   675         684         693         702
ATT CAT TTT GAT GAC TTT TCT CTC GAC GTT GAT GCC ATG ATC ACA GCT GCT CTC
 I   H   F   D   D   F   S   L   D   V   D   A   M   I   T   A   A   L 711         720   729         738         747         756
CGG ATG TTC ATG GAG CTG GGG ATG GTA CAG AAA TTT AAA ATT GAC TAT GAG ACA
 R   M   F   M   E   L   G   M   V   Q   K   F   K   I   D   Y   E   T
```

FIGURE 1B

```
      765         774         783         792     801         810
CTG TGT AGG TGG CTT ACA GTG AGG AAA AAC TAT CGG ATG GTT CTA TAC CAC
 L   C   R   W   L   T   V   R   K   N   Y   R   M   V   L   Y   H 819         828         837         846     855         864
AAC TGG AGA CAT GCC TTC AAC GTG TGT CAG CTG ATG TTC GCG ATG TTA ACC ACT
 N   W   R   H   A   F   N   V   C   Q   L   M   F   A   M   L   T   T 873         882         891         900     909         918
GCT GGG TTT CAA GAC ATT CTG ACC GAG GTG GAA ATT TTA GCG GTG ATT GTG GGA
 A   G   F   Q   D   I   L   T   E   V   E   I   L   A   V   I   V   G 927         936         945         954     963         972
TGC CTG TGT CAT GAC CTC GAC CAC AGG GGA ACC AAC AAT GCC TTC CAA GCT AAG
 C   L   C   H   D   L   D   H   R   G   T   N   N   A   F   Q   A   K 981         990         999        1008    1017        1026
AGT GGC TCT GCC CTG GCC CAA CTC TAT GGA ACC TCT GCT ACC TTG GAG CAT CAC
 S   G   S   A   L   A   Q   L   Y   G   T   S   A   T   L   E   H   H 1035        1044        1053        1062    1071        1080
CAT TTC AAC CAC GCC GTG ATG ATC CTT CAA AGT GAG GGT CAC AAT ATC TTT GCT
 H   F   N   H   A   V   M   I   L   Q   S   E   G   H   N   I   F   A 1089        1098        1107        1116    1125        1134
AAC CTG TCC TCC AAG GAA TAT AGT GAC CTT ATG CAG CTT TTG AAG CAG TCA ATA
 N   L   S   S   K   E   Y   S   D   L   M   Q   L   L   K   Q   S   I
```

FIGURE 1C

```
        1143            1152            1161           1170           1179          1188
TTG GCA ACA GAC CTC ACG CTG TAC TTT GAG AGG AGA ACT GAA TTC TTT GAA CTT
 L   A   T   D   L   T   L   Y   F   E   R   R   T   E   F   F   E   L 1197            1206            1215           1224           1233          1242
GTC AGT AAA GGA GAA TAC GAT TGG AAC ATC AAA AAC CAT CGT GAT ATA TTT CGA
 V   S   K   G   E   Y   D   W   N   I   K   N   H   R   D   I   F   R 1251            1260            1269           1278           1287          1296
TCA ATG TTA ATG ACA GCC TGT GAC CTT GGA GCC GTG ACC AAA CCG TGG GAG ATC
 S   M   L   M   T   A   C   D   L   G   A   V   T   K   P   W   E   I 1305            1314            1323           1332           1341          1350
TCC AGA CAG GTG GCA GAA CTT GTA ACC AGT GAG TTC TTC GAA CAA GGA GAT CGG
 S   R   Q   V   A   E   L   V   T   S   E   F   F   E   Q   G   D   R 1359            1368            1377           1386           1395          1404
GAG AGA TTA GAG CTC AAA CTC ACT CCT TCA GCA ATT TTT GAT CGG AAC CGG AAG
 E   R   L   E   L   K   L   T   P   S   A   I   F   D   R   N   R   K 1413            1422            1431           1440           1449          1458
GAT GAA CTG CCT CGG TTG CAA CTG GAG TGG ATT GAT AGC ATC TGC ATG CCT TTG
 D   E   L   P   R   L   Q   L   E   W   I   D   S   I   C   M   P   L 1467            1476            1485           1494           1503          1512
TAT CAG GCA CTG GTG AAG GTC AAC GTG AAA CTG AAG CCG ATG CTA GAT TCA GTA
 Y   Q   A   L   V   K   V   N   V   K   L   K   P   M   L   D   S   V
```

FIGURE 1D

```
        1521            1530            1539            1548            1557            1566
GCT ACA AAC AGA AGT AAG TGG GAA GAG CTA CAC CAA AAA CGA CTG GCC TCA
 A   T   N   R   S   K   W   E   E   L   H   Q   K   R   L   A   S 1575            1584            1593            1602            1611            1620
ACT GCC TCA TCC TCC CCT GCC AGT GTT ATG GTA GCC AAG GAA GAC AGG AAC
 T   A   S   S   S   P   A   S   V   M   V   A   K   E   D   R   N 1629            1638            1647            1656            1665            1674
TAA ACC TCC AGG TCA GCT GCA AAA TGA CTA CAG CCT GAA GGG CCA TTT 1683            1692            1701            1710            1719            1728
TCA GTC CAG CAA TGT CAT CCT TTT GTT CTT TTA GCT CAG AAA GAC CTA ACA TCT 1737            1746            1755            1764            1773            1782
CAA GGA TGC ACT GGG AAC CAT GCC TGG GCT TTC ACC TTG AAG CAT GGT CAG CAG

CA 3'
```

FIGURE 1E

```
5' TCG ACG TGG AAA GAT GTT ACT TCA TCT CCC AGG TTT GCT CAC TGC AAA TAC AAT
      9          18          27          36          45          54

CCT GAG AAC TGA ACT AGG GCC TTA AAG TCC TGA CAT GCA TGG CTT GGT TTT GTG
     63          72          81          90          99         108

GAT TGC CTC TCT CAA CAG GTG AAA TTT ACC AAA TCC TTT GAA TTG ATG TCC
    117         126         135         144         153         162
                                                             M   S

CCA AAG TGC AGT GCT GAT GCT GAG AAC AGT TTC AAA GAA AGC ATG GAG AAA TCA
    171         180         189         198         207         216
     P   K   C   S   A   D   A   E   N   S   F   K   E   S   M   E   K   S

TCA TAC TCC GAC TGG CTA ATA AAT AAC AGC ATT GCT GAG CTG GTT GCT TCA ACA
    225         234         243         252         261         270
     S   Y   S   D   W   L   I   N   N   S   I   A   E   L   V   A   S   T

GGC CTT CCA GTG AAC ATC AGT GAT GCC TAC CAG GAT CCG CGC TTT GAT GCA GAG
    279         288         297         306         315         324
     G   L   P   V   N   I   S   D   A   Y   Q   D   P   R   F   D   A   E

GCA GAC CAG ATA TCT GGT TTT CAC ATA AGA TCT GTT CTT TGT GTC CCT ATT TGG
    333         342         351         360         369         378
     A   D   Q   I   S   G   F   H   I   R   S   V   L   C   V   P   I   W

FIGURE 2A
```

```
387            396        405        414        423        432
AAT AGC AAC CAC CAA ATA ATT GGA GTG GCT CAA GTG TTA AAC AGA CTT GAT GGG
 N   S   N   H   Q   I   I   G   V   A   Q   V   L   N   R   L   D   G 441            450        459        468        477        486
AAA CCT TTT GAT GAT GCA GAT CAA CGA CTT TTT GAG GCT TTT GTC ATC TTT TGT
 K   P   F   D   D   A   D   Q   R   L   F   E   A   F   V   I   F   C 495            504        513        522        531        540
GGA CTT GGC ATC AAC ACA ATT ATG TAT GAT CAA GTG AAG TCC TGG GCC
 G   L   G   I   N   T   I   M   Y   D   Q   V   K   S   W   A 549            558        567        576        585        594
AAG CAG TCT GTG GCT CTT GAT GTG CTA TCA TAC CAT GCA ACA TGT TCA AAA GCT
 K   Q   S   V   A   L   D   V   L   S   Y   H   A   T   C   S   K   A 603            612        621        630        639        648
GAA GTT GAC AAG TTT AAG GCA GCC AAC ATC CCT CTG GTG TCA GAA CTT GCC ATC
 E   V   D   K   F   K   A   A   N   I   P   L   V   S   E   L   A   I 657            666        675        684        693        702
GAT GAC ATT CAT TTT GAT GAC TTT TCT CTC GAC GTT GAT GCC ATG ATC ACA GCT
 D   D   I   H   F   D   D   F   S   L   D   V   D   A   M   I   T   A 711            720        729        738        747        756
GCT CTC CGG ATG TTC ATG GAG CTG GGG ATG GTA CAG AAA TTT AAA ATT GAC TAT
 A   L   R   M   F   M   E   L   G   M   V   Q   K   F   K   I   D   Y
```

FIGURE2B

```
GAG ACA CTG TGT AGG TGG CTT TTG ACA GTG AGG AAA AAC TAT CGG ATG GTT CTA
 E   T   L   C   R   W   L   L   T   V   R   K   N   Y   R   M   V   L
765         774             783             792             801     810

TAC CAC AAC TGG AGA CAT GCC TTC AAC GTG TGT CAG CTG ATG TTC GCG ATG TTA
 Y   H   N   W   R   H   A   F   N   V   C   Q   L   M   F   A   M   L
819         828             837             846             855     864

ACC ACT GCT GGG TTT CAA GAC ATT CTG ACC GAG GTG GAA ATT TTA GCG GTG ATT
 T   T   A   G   F   Q   D   I   L   T   E   V   E   I   L   A   V   I
873         882             891             900             909     918

GTG GGA TGC CTG TGT CAT GAC CTC GAC CAC AGG GGA ACC AAC AAT GCC TTC CAA
 V   G   C   L   C   H   D   L   D   H   R   G   T   N   N   A   F   Q
927         936             945             954             963     972

GCT AAG AGT GGC TCT GCC CTG GCC CTG TAT CTT CAA AGT GAG GGT CAC TTG GAG
 A   K   S   G   S   A   L   A   L   Y   L   Q   S   E   G   H   L   E
981         990             999             1008            1017    1026

CAT CAC CAT TTC AAC CAC GCC GTG ATG ATC CTT CAA AGT GAG GGT CAC AAT ATC
 H   H   H   F   N   H   A   V   M   I   L   Q   S   E   G   H   N   I
1035        1044            1053            1062            1071    1080

TTT GCT AAC CTG TCC TCC AAG GAA TAT AGT GAC CTT ATG CAG CTT TTG AAG CAG
 F   A   N   L   S   S   K   E   Y   S   D   L   M   Q   L   L   K   Q
1089        1098            1107            1116            1125    1134

FIGURE2C
```

```
       1143            1152            1161            1170            1179            1188
TCA ATA TTG GCA ACA GAC CTC ACG CTG TAC TTT GAG GAG AAG GTC AGA AAT ACA
 S   I   L   A   T   D   L   T   L   Y   F   E   E   K   V   R   N   T 1197            1206            1215            1224            1233            1242
TCA CCT GGA GCT GTG AAC CAC CTA CCT GGC ACA CCT GGC ACA AGC AAT CTG CAG CTC TTC TTT
 S   P   G   A   V   N   H   L   P   G   T   S   N   L   Q   L   F   F 1251            1260            1269            1278            1287            1296
GGA GCA CCC CCT TAT TGA TGA TGG AAA GAA CCC TGT CTG TGT CTG CCT TGA TAC
 G   A   P   P   Y 1305            1314            1323            1332            1341            1350
TTG GTA TTG CCT TGG TAC AGC AGC CTG TGA TGC TGT TAC ATA GCA TGA GGG CTG 1359            1368            1377            1386            1395            1404
CTG GCC CCA CTG TCC ATA CAC TTA CAA CAT GAA AAG CTA TCT GGC CCA AAG GTT 1413            1422            1431            1440            1449            1458
TAT GCT ACA CAT AGT TTA CAA AGA TTA TCT CAG AGG GCA GAA CCG GGA GGC TGG 1467            1476            1485            1494            1503            1512
GGA CTT ATA ATC TAC CCA GAA GGA AAA GTT CTT CCT TAT AGA AGA TTT CAA TTA
```

FIGURE 2D

```
      1521      1530      1539      1548      1557      1566
ACA CAC ATG GAA AGG TGG AAA AAT CAT CAG CTG GCA AAT ACC ACG GTA 1575      1584      1593      1602      1611      1620
GTA ATT TTT ATT GGC AAC AAT AAA TCT TTC TGT AAC TGC CCT GGG ACC TTG AAC 1629      1638      1647      1656      1665      1674
AAG TCA CTT CAC CTT CCT TCA CCT TGA GTT TCC TCA CCT ATA AAA TGA GAG AAT 1683      1692      1701      1710      1719      1728
TAA TAG GAG ATT TTT CTC AAA AGT TCC ATA CAG CCC TAC CAG TCT ATA ACT ATA 1737      1746      1755      1764      1773      1782
ATG AAA ATT CAA ACA TAG AAA AGA AGT CAT TCT ATG ACC CAG CAA TTT TAC ATA 1791      1800      1809      1818      1827      1836
TAC ATG TAC ATA TTC ATA TAC ACA GAG AGA GAG AAC TCA CAC AAA TTC ACA AGG
```

FIGURE 2E

```
1845            1854            1863            1872            1881            1890
AAA CAT GTA CAA GGT GGT TCA TAG CTG CAT TGT ATG TAA TAG CAA GAA ATA TTA 1899            1908            1917            1926            1935            1944
GAA AAA TAT AAA TTT TCA TCT TCC AGG AAA TGG GTA AAT AGA CAG TGG TAT AAT 1953            1962            1971            1980
AAT AGA TGG AAA TAG CAT ACA TCA GTA TGA AGG AAT GG 3'
```

FIGURE 2F

```
  1   M S — — — — — — — — — — — — — — — — — — — — — — — — — — — — — —   HSPDE10A1
  1   M S — — — — — — — — — — — — — — — — — — — — — — — — — — — — — —   HSPDE10A2
  1   M E R A G P S F G Q Q R G Q Q P Q Q Q K Q Q Q R D Q D S V           HPDE5A1

3   — — — — — — — — — — — — — — — — — — — — — — — — — — — — — —       HSPDE10A1
  3   — — — — — — — — — — — — — — — — — — — — — — — — — — — — — —       HSPDE10A2
 31   E A W L D D H W D F T F S Y F V R K A T R E M V N A W F A E         HPDE5A1

3   — — — — — — — P K C S — — — — — — — — — — — — — — — — — — —       HSPDE10A1
  3   — — — — — — — P K C S — — — — — — — — — — — — — — — — — — —       HSPDE10A2
 61   R V H T I P V C K E G I R G H T E S C S C P L Q Q S P R A D         HPDE5A1

7   — — — — — — — — — — — — — — — — — — — — — — — — — — A D A         HSPDE10A1
  7   — — — — — — — — — — — — — — — — — — — — — — — — — — A D A         HSPDE10A2
 91   N S V P G T P T R K I S A S E F D R P L R P I V V K D S E G         HPDE5A1

10   E N S F K E S M E K S S — — — — — — — — — — — — — — — — — —       HSPDE10A1
 10   E N S F K E S M E K S S — — — — — — — — — — — — — — — — — —       HSPDE10A2
121   T V S F L S D S E K K E Q M P L T P P R F D H D E G D Q C S         HPDE5A1

22   — — — — — — — — — — — — — — — — — — — — — — — — — — — — — —       HSPDE10A1
 22   — — — — — — — — — — — — — — — — — — — — — — — — — — — — — —       HSPDE10A2
151   R L L E L V K D I S S H L D V T A L C H K I F L H I H G L I         HPDE5A1
```

FIGURE 3A

```
 22 ------YSDWLI------------------------------------------------  HSPDE10A1
 22 ------YSDWLI------------------------------------------------  HSPDE10A2
181 SADRYSLFLVCEDSSNDKFLISRLFDVAEG                                HPDE5A1

28 ---------------------------NNSIAELVASTGLPV                    HSPDE10A1
 28 ---------------------------NNSIAELVASTGLPV                    HSPDE10A2
211 STLEEVSNNCIRLEWNKGIVGHVAALGEPL                                HPDE5A1

43 NISDAYQDPRFDAEADQISGFHIRSVLCVP                                HSPDE10A1
 43 NISDAYQDPRFDAEADQISGFHIRSVLCVP                                HSPDE10A2
241 NIKDAYEDPRFNAEVDQITGYKTQSILCMP                                HPDE5A1

73 I-----------------------------                                HSPDE10A1
 73 I-----------------------------                                HSPDE10A2
271 IKNHREEVVGVAQAINKKSGNGGTFTEKDE                                HPDE5A1

74 ------------------------------                                HSPDE10A1
 74 ------------------------------                                HSPDE10A2
301 KDFAAYLAFCGIVLHNAQLYETSLLENKRN                                HPDE5A1

74 ------------------------------                                HSPDE10A1
 74 ------------------------------                                HSPDE10A2
331 QVLLDLASLIFEEQQSLEVILKKIAATIIS                                HPDE5A1
```

FIGURE 3B

```
 74  - - - - - - - - - - - - - - - - - - - - - - - - - - - - - - -                          HSPDE10A1
 74  - - - - - - - - - - - - - - - - - - - - - - - - - - - - - - -                          HSPDE10A2
361  F M Q V Q K C T I F I V D E D C S D S F S S V F H M E C E E                             HPDE5A1

74  - - - - - - - - - - - - - - - - - - - - - - - - - - - - - - -                          HSPDE10A1
 74  - - - - - - - - - - - - - - - - - - - - - - - - - - - - - - -                          HSPDE10A2
391  L E K S S D T L T R E H D A N K I N Y M Y A Q Y V K N T M E                             HPDE5A1

74  - - - - - - - - - - - - - - W N S N H - - - - - - - - - - - -                          HSPDE10A1
 74  - - - - - - - - - - - - - - W N S N H - - - - - - - - - - - -                          HSPDE10A2
421  P L N I P D V S K D K R F P W T T E N T G N V N Q Q C I R S                             HPDE5A1

79  - - - - - - - - - - - - - - Q I I G V A Q V L N R L D G - - -                          HSPDE10A1
 79  - - - - - - - - - - - - - - Q I I G V A Q V L N R L D G - - -                          HSPDE10A2
451  L L C T P I K N G K K N K V I G V C Q L V N K M E E N T G K                             HPDE5A1

93  - K P F D D A D Q R L F E A F V I F C G L G I N N T I M Y D                             HSPDE10A1
 93  - K P F D D A D Q R L F E A F V I F C G L G I N N T I M Y D                             HSPDE10A2
481  V K P F N R N D E Q F L E A F V I F C G L G I Q N T Q M Y E                             HPDE5A1

122  Q V K K S W A K Q S V A L D V L S Y H A T C S K A E - - - V                             HSPDE10A1
122  Q V K K S W A K Q S V A L D V L S Y H A T C S K A E - - - V                             HSPDE10A2
511  A V E R A M A K Q M V T L E V L S Y H A S A A E E T R E L                               HPDE5A1
```

FIGURE 3C

```
149  D K F K A A N I P L V S E L A I D D I H F D D F S L D V D A   HSPDE10A1
149  D K F K A A N I P L V S E L A I D D I H F D D F S L D V D A   HSPDE10A2
541  Q S L A A V V P S A Q T L K I T D F S F S D F E L S D L E     HPDE5A1

179  M I T A A L R M F M E L G M V Q K F K I D Y E T L C R W L L   HSPDE10A1
179  M I T A A L R M F M E L G M V Q K F K I D Y E T L C R W L L   HSPDE10A2
571  T A L C T I R M F T D L N L V Q N F Q M K H E V L C R W I L   HPDE5A1

209  T V R K N Y R M - - V L Y H N W R H A F N V C Q L M F A M L T HSPDE10A1
209  T V R K N Y R M - - V L Y H N W R H A F N V C Q L M F A M L T HSPDE10A2
601  S V K K N Y R K N V A Y H N W R H A F N T A Q C M F A A L K   HPDE5A1

238  T A G F Q D I L T E V E I L A V I V G C L C H D L D H R G T   HSPDE10A1
238  T A G F Q D I L T E V E I L A V I V G C L C H D L D H R G T   HSPDE10A2
631  A G K I Q N K L T D L E I L A L L I A A L S H D L D H R G V   HPDE5A1

268  N N A F Q A K S G S A L A Q L Y G T S A T L E H H H H F N H A HSPDE10A1
268  N N A F Q A K S G S A L A Q L Y G T S A T L E H H H H F N H A HSPDE10A2
661  N N S Y I Q R S E H P L A Q L Y C H S - I M E H H H H F D Q C HPDE5A1

298  V M I L Q S E G H N I F A N L S S K E Y S D L M Q L L K Q S   HSPDE10A1
298  V M I L Q S E G H N I F A N L S S K E Y S D L M Q L L K Q S   HSPDE10A2
690  L M I L N S P G N Q I L S G L S I E Y K T T L K I I K Q A     HPDE5A1
```

FIGURE 3D

```
328  ILATDLTLYFERRTEFFELVSKGEYDWNIK                HSPDE10A1
328  ILATDLTLYFEEK-------------VR                  HSPDE10A2
720  ILATDLALYIKRRGEFFELIRKNQFNLEDP                HPDE5A1

358  NHRDIFRSMLMTACDLGAVTKPWEISRQVA                HSPDE10A1
343  NTSPGAVNHLPGTSNL-------------                 HSPDE10A2
750  HQKELFLAMLMTACDLSAITKPWPIQQRIA                HPDE5A1

388  ELVTSEFFEQGDRERLELKLTPSAIFDRNR                HSPDE10A1
359  QL---FFGA--------------------                 HSPDE10A2
780  ELVATEFFDQGDRERKELNIEPTDLMNREK                HPDE5A1

418  KDELPRLQLEWIDSICMPLYQALVKVNVKL                HSPDE10A1
365  -------------PPY-------------                 HSPDE10A2
810  KNKIPSMQVGFIDAICLQLYEALTHVSEDC                HPDE5A1

448  KPMLDSVATNRSKWEEL--HQKRLLASTAS                HSPDE10A1
367  -----------------------------                 HSPDE10A2
840  FPLLDGCRKNRQKWQALAEQQEKMLINGES                HPDE5A1

476  SSSPASVMVAKEDRN                               HSPDE10A1
367  ---------------                               HSPDE10A2
870  G---------QAKRN                               HPDE5A1
```

FIGURE 3E

FIGURE 7

| Tissue Category | Clones | Libs | Abs Abund | % Abund |
|---|---|---|---|---|
| Cardiovascular System | 253105 | 0/64 | 0 | 0.0000 |
| Connective Tissue | 134008 | 0/41 | 0 | 0.0000 |
| Digestive System | 447016 | 0/130 | 0 | 0.0000 |
| Embryonic Structures | 106591 | 0/21 | 0 | 0.0000 |
| Endocrine System | 210781 | 0/50 | 0 | 0.0000 |
| Exocrine Glands | 252458 | 0/61 | 0 | 0.0000 |
| Genitalia, Female | 392343 | 0/92 | 0 | 0.0000 |
| Genitalia, Male | 430286 | 2/109 | 2 | 0.0005 |
| Germ Cells | 36677 | 0/5 | 0 | 0.0000 |
| Hemic and Immune System | 662225 | 0/153 | 0 | 0.0000 |
| Liver | 92176 | 0/25 | 0 | 0.0000 |
| Musculoskeletal System | 154504 | 0/44 | 0 | 0.0000 |
| Nervous System | 904527 | 1/185 | 1 | 0.0001 |
| Pancreas | 100545 | 0/21 | 0 | 0.0000 |
| Respiratory System | 362922 | 0/83 | 0 | 0.0000 |
| Sense Organs | 19253 | 0/8 | 0 | 0.0000 |
| Skin | 72082 | 0/15 | 0 | 0.0000 |
| Stomatognathic System | 10988 | 0/4 | 0 | 0.0000 |
| Unclassified/Mixed | 103494 | 0/8 | 0 | 0.0000 |
| Urinary Tract | 252077 | 0/57 | 0 | 0.0000 |
| Totals | 4998058 | 3/1176 | 3 | 0.0000 |

| Library | Clones | Description | Abs Abund | % Abund |
|---|---|---|---|---|
| HNT2TXC01 | 2068 | hNT2 teratoCA | 1 | 0.0484 |
| PROSTMC01 | 3899 | prostate(adenoCA) 55 | 1 | 0.0256 |
| PROSNOT06 | 8828 | prostate(adenoCA) 57 | 1 | 0.0113 |

SEQUENCE LISTING

<160> NUMBER OF SEQ ID NOS: 7

<210> SEQ ID NO 1
<211> LENGTH: 490
<212> TYPE: PRT
<213> ORGANISM: HOMO SAPIENS
<223> OTHER INFORMATION: HSPDE10A1

<400> SEQUENCE: 1

Met Ser Pro Lys Cys Ser Ala Asp Ala Glu Asn Ser Phe Lys Glu Ser
1               5                   10                  15

Met Glu Lys Ser Ser Tyr Ser Asp Trp Leu Ile Asn Asn Ser Ile Ala
            20                  25                  30

-continued

```
Glu Leu Val Ala Ser Thr Gly Leu Pro Val Asn Ile Ser Asp Ala Tyr
         35                  40                  45
Gln Asp Pro Arg Phe Asp Ala Glu Ala Asp Gln Ile Ser Gly Phe His
     50                  55                  60
Ile Arg Ser Val Leu Cys Val Pro Ile Trp Asn Ser Asn His Gln Ile
 65                  70                  75                  80
Ile Gly Val Ala Gln Val Leu Asn Arg Leu Asp Gly Lys Pro Phe Asp
                 85                  90                  95
Asp Ala Asp Gln Arg Leu Phe Glu Ala Phe Val Ile Phe Cys Gly Leu
            100                 105                 110
Gly Ile Asn Asn Thr Ile Met Tyr Asp Gln Val Lys Lys Ser Trp Ala
            115                 120                 125
Lys Gln Ser Val Ala Leu Asp Val Leu Ser Tyr His Ala Thr Cys Ser
        130                 135                 140
Lys Ala Glu Val Asp Lys Phe Lys Ala Ala Asn Ile Pro Leu Val Ser
145                 150                 155                 160
Glu Leu Ala Ile Asp Asp Ile His Phe Asp Asp Phe Ser Leu Asp Val
                165                 170                 175
Asp Ala Met Ile Thr Ala Ala Leu Arg Met Phe Met Glu Leu Gly Met
            180                 185                 190
Val Gln Lys Phe Lys Ile Asp Tyr Glu Thr Leu Cys Arg Trp Leu Leu
        195                 200                 205
Thr Val Arg Lys Asn Tyr Arg Met Val Leu Tyr His Asn Trp Arg His
        210                 215                 220
Ala Phe Asn Val Cys Gln Leu Met Phe Ala Met Leu Thr Thr Ala Gly
225                 230                 235                 240
Phe Gln Asp Ile Leu Thr Glu Val Glu Ile Leu Ala Val Ile Val Gly
                245                 250                 255
Cys Leu Cys His Asp Leu Asp His Arg Gly Thr Asn Asn Ala Phe Gln
            260                 265                 270
Ala Lys Ser Gly Ser Ala Leu Ala Gln Leu Tyr Gly Thr Ser Ala Thr
        275                 280                 285
Leu Glu His His His Phe Asn His Ala Val Met Ile Leu Gln Ser Glu
        290                 295                 300
Gly His Asn Ile Phe Ala Asn Leu Ser Ser Lys Glu Tyr Ser Asp Leu
305                 310                 315                 320
Met Gln Leu Leu Lys Gln Ser Ile Leu Ala Thr Asp Leu Thr Leu Tyr
                325                 330                 335
Phe Glu Arg Arg Thr Glu Phe Phe Glu Leu Val Ser Lys Gly Glu Tyr
            340                 345                 350
Asp Trp Asn Ile Lys Asn His Arg Asp Ile Phe Arg Ser Met Leu Met
        355                 360                 365
Thr Ala Cys Asp Leu Gly Ala Val Thr Lys Pro Trp Glu Ile Ser Arg
        370                 375                 380
Gln Val Ala Glu Leu Val Thr Ser Glu Phe Phe Glu Gln Gly Asp Arg
385                 390                 395                 400
Glu Arg Leu Glu Leu Lys Leu Thr Pro Ser Ala Ile Phe Asp Arg Asn
                405                 410                 415
Arg Lys Asp Glu Leu Pro Arg Leu Gln Leu Glu Trp Ile Asp Ser Ile
            420                 425                 430
Cys Met Pro Leu Tyr Gln Ala Leu Val Lys Val Asn Val Lys Leu Lys
        435                 440                 445
```

```
Pro Met Leu Asp Ser Val Ala Thr Asn Arg Ser Lys Trp Glu Glu Leu
    450                 455                 460

His Gln Lys Arg Leu Leu Ala Ser Thr Ala Ser Ser Ser Pro Ala
465                 470                 475                 480

Ser Val Met Val Ala Lys Glu Asp Arg Asn
                485                 490

<210> SEQ ID NO 2
<211> LENGTH: 1784
<212> TYPE: DNA
<213> ORGANISM: HOMO SAPIENS
<223> OTHER INFORMATION: HSPDE10A1

<400> SEQUENCE: 2
tggaaagatg ttacttcatc tcccaggttt gctcactgca aatacaatcc tgagaactga      60
actagggcct taaagtcctg acatgcatgg cttggttttg tggattgcct ctctcaacag     120
gtggtgaaat ttaccaaatc ctttgaattg atgtccccaa agtgcagtgc tgatgctgag     180
aacagtttca agaaaagcat ggagaaatca tcatactccg actggctaat aaataacagc     240
attgctgagc tggttgcttc aacaggcctt ccagtgaaca tcagtgatgc ctaccaggat     300
ccgcgctttg atgcagaggc agaccagata tctggttttc acataagatc tgttctttgt     360
gtccctattt ggaatagcaa ccaccaaata attggagtgg ctcaagtgtt aaacagactt     420
gatgggaaac cttttgatga tgcagatcaa cgacttttg aggcttttgt catcttttgt      480
ggacttggca tcaacaacac aattatgtat gatcaagtga agaagtcctg ggccaagcag     540
tctgtggctc ttgatgtgct atcataccat gcaacatgtt caaaagctga agttgacaag     600
tttaaggcag ccaacatccc tctggtgtca gaacttgcca tcgatgacat tcattttgat     660
gactttctc tcgacgttga tgccatgatc acagctgctc tccggatgtt catggagctg     720
gggatggtac agaaatttaa aattgactat gagacactgt gtaggtggct tttgacagtg     780
aggaaaaact atcggatggt tctataccac aactggagac atgccttcaa cgtgtgtcag     840
ctgatgttcg cgatgttaac cactgctggg tttcaagaca ttctgaccga ggtggaaatt     900
ttagcggtga ttgtgggatg cctgtgtcat gacctcgacc acaggggaac caacaatgcc     960
ttccaagcta agagtggctc tgccctggcc caactctatg gaacctctgc taccttggag    1020
catcaccatt tcaaccacgc cgtgatgatc cttcaaagtg agggtcacaa tatctttgct    1080
aacctgtcct ccaaggaata tagtgacctt atgcagcttt tgaagcagtc aatattggca    1140
acagacctca cgctgtactt tgagaggaga actgaattct ttgaacttgt cagtaaagga    1200
gaatacgatt ggaacatcaa aaaccatcgt gatatattc gatcaatgtt aatgacagcc    1260
tgtgaccttg agccgtgac caaaccgtgg gagatctcca gacaggtggc agaacttgta    1320
accagtgagt tcttcgaaca aggagatcgg gagagattag agctcaaact cactccttca    1380
gcaattttg atcggaaccg gaaggatgaa ctgcctcggt tgcaactgga gtggattgat    1440
agcatctgca tgcctttgta tcaggcactg gtgaaggtca acgtgaaact gaagccgatg    1500
ctagattcag tagctacaaa cagaagtaag tgggaagagc tacaccaaaa acgactgctg    1560
gcctcaactg cctcatcctc ctcccctgcc agtgttatgg tagccaagga agacaggaac    1620
taaacctcca ggtcagctgc agctgcaaaa tgactacagc ctgaagggcc attttcagtc    1680
cagcaatgtc atcctttgt tcttttagct cagaaagacc taacatctca aggatgcact    1740
gggaaccatg cctgggcttt caccttgaag catggtcagc agca                     1784
```

```
<210> SEQ ID NO 3
<211> LENGTH: 367
<212> TYPE: PRT
<213> ORGANISM: HOMO SAPIENS
<223> OTHER INFORMATION: HSPDE10A2

<400> SEQUENCE: 3
```

| | | | | | | | | | | | | | | |
|---|---|---|---|---|---|---|---|---|---|---|---|---|---|---|
|Met|Ser|Pro|Lys|Cys|Ser|Ala|Asp|Ala|Glu|Asn|Ser|Phe|Lys|Glu|Ser|
|1| | | |5| | | | |10| | | | |15| |

Met Ser Pro Lys Cys Ser Ala Asp Ala Glu Asn Ser Phe Lys Glu Ser
1               5                   10                  15

Met Glu Lys Ser Ser Tyr Ser Asp Trp Leu Ile Asn Asn Ser Ile Ala
            20                  25                  30

Glu Leu Val Ala Ser Thr Gly Leu Pro Val Asn Ile Ser Asp Ala Tyr
            35                  40                  45

Gln Asp Pro Arg Phe Asp Ala Glu Ala Asp Gln Ile Ser Gly Phe His
        50                  55                  60

Ile Arg Ser Val Leu Cys Val Pro Ile Trp Asn Ser Asn His Gln Ile
65                  70                  75                  80

Ile Gly Val Ala Gln Val Leu Asn Arg Leu Asp Gly Lys Pro Phe Asp
                85                  90                  95

Asp Ala Asp Gln Arg Leu Phe Glu Ala Phe Val Ile Phe Cys Gly Leu
                100                 105                 110

Gly Ile Asn Asn Thr Ile Met Tyr Asp Gln Val Lys Lys Ser Trp Ala
            115                 120                 125

Lys Gln Ser Val Ala Leu Asp Val Leu Ser Tyr His Ala Thr Cys Ser
        130                 135                 140

Lys Ala Glu Val Asp Lys Phe Lys Ala Ala Asn Ile Pro Leu Val Ser
145                 150                 155                 160

Glu Leu Ala Ile Asp Asp Ile His Phe Asp Asp Phe Ser Leu Asp Val
                165                 170                 175

Asp Ala Met Ile Thr Ala Ala Leu Arg Met Phe Met Glu Leu Gly Met
                180                 185                 190

Val Gln Lys Phe Lys Ile Asp Tyr Glu Thr Leu Cys Arg Trp Leu Leu
            195                 200                 205

Thr Val Arg Lys Asn Tyr Arg Met Val Leu Tyr His Asn Trp Arg His
210                 215                 220

Ala Phe Asn Val Cys Gln Leu Met Phe Ala Met Leu Thr Thr Ala Gly
225                 230                 235                 240

Phe Gln Asp Ile Leu Thr Glu Val Glu Ile Leu Ala Val Ile Val Gly
                245                 250                 255

Cys Leu Cys His Asp Leu Asp His Arg Gly Thr Asn Asn Ala Phe Gln
                260                 265                 270

Ala Lys Ser Gly Ser Ala Leu Ala Gln Leu Tyr Gly Thr Ser Ala Thr
        275                 280                 285

Leu Glu His His Phe Asn His Ala Val Met Ile Leu Gln Ser Glu
        290                 295                 300

Gly His Asn Ile Phe Ala Asn Leu Ser Ser Lys Glu Tyr Ser Asp Leu
305                 310                 315                 320

Met Gln Leu Leu Lys Gln Ser Ile Leu Ala Thr Asp Leu Thr Leu Tyr
                325                 330                 335

Phe Glu Glu Lys Val Arg Asn Thr Ser Pro Gly Ala Val Asn His Leu
            340                 345                 350

Pro Gly Thr Ser Asn Leu Gln Leu Phe Phe Gly Ala Pro Pro Tyr
            355                 360                 365

```
<210> SEQ ID NO 4
```

<211> LENGTH: 1982
<212> TYPE: DNA
<213> ORGANISM: HOMO SAPIENS
<223> OTHER INFORMATION: HSPDE10A2

<400> SEQUENCE: 4

```
tcgacgtgga aagatgttac ttcatctccc aggtttgctc actgcaaata caatcctgag     60
aactgaacta gggccttaaa gtcctgacat gcatggcttg gttttgtgga ttgcctctct    120
caacaggtgg tgaaatttac caaatccttt gaattgatgt ccccaaagtg cagtgctgat    180
gctgagaaca gtttcaaaga aagcatggag aaatcatcat actccgactg ctaataaat    240
aacagcattg ctgagctggt tgcttcaaca ggccttccag tgaacatcag tgatgcctac    300
caggatccgc gctttgatgc agaggcagac cagatatctg gttttcacat aagatctgtt    360
ctttgtgtcc ctatttggaa tagcaaccac caataattg gagtggctca agtgttaaac    420
agacttgatg ggaaaccttt tgatgatgca gatcaacgac tttttgaggc ttttgtcatc    480
ttttgtggac ttggcatcaa caacacaatt atgtatgatc aagtgaagaa gtcctgggcc    540
aagcagtctg tggctcttga tgtgctatca taccatgcaa catgttcaaa agctgaagtt    600
gacaagttta aggcagccaa catccctctg gtgtcagaac ttgccatcga tgacattcat    660
tttgatgact tttctctcga cgttgatgcc atgatcacac tgctctccg gatgttcatg    720
gagctgggga tggtacagaa atttaaaatt gactatgaga cactgtgtag gtggcttttg    780
acagtgagga aaaactatcg gatggttcta taccacaact ggagacatgc cttcaacgtg    840
tgtcagctga tgttcgcgat gttaaccact gctgggtttc aagacattct gaccgaggtg    900
gaaattttag cggtgattgt gggatgcctg tgtcatgacc tcgaccacag gggaaccaac    960
aatgccttcc aagctaagag tggctctgcc ctggcccaac tctatggaac ctctgctacc   1020
ttggagcatc accatttcaa ccacgccgtg atgatcctc aaagtgaggg tcacaatatc   1080
tttgctaacc tgtcctccaa ggaatatagt gaccttatgc agcttttgaa gcagtcaata   1140
ttggcaacag acctcacgct gtactttgag gagaaggtca gaaatacatc acctggagct   1200
gtgaaccacc tacctggcac aagcaatctg cagctcttct ttggagcacc cccttattga   1260
tgatggaaag aaccctgtct gtgtctgcct tgatacttgg tattgccttg gtacagcagc   1320
ctgtgatgct gttacatagc atgagggctg ctggccccac tgtccatata cttacaacat   1380
gaaaagctat ctggcccaaa ggtttatgct acacatagtt tacaaagatt atctcagagg   1440
gcagaaccgg gaggctgggg acttataatc tacccagaag gaaaagttct tccttataga   1500
agatttcaat taacacacat ggaaaggtgg aaatggaaaa atcatcagct ggcaaatacc   1560
acggtagtaa ttttttattgg caacaataaa tctttctgta actgccctgg gaccttgaac   1620
aagtcacttc accttccttc accttgagtt tcctcaccta taaatgaga gaattaatag   1680
gagatttttc tcaaaagttc catacagccc taccagtcta taactataat gaaaattcaa   1740
acatagaaaa gaagtcattc tatgacccag caattttaca tatacatgta catattcata   1800
tacacagaga gagagaactc acacaaattc acaaggaaac atgtacaagg tggttcatag   1860
ctgcattgta tgtaatagca agaaatatta gaaaatatata aattttcatc ttccaggaaa   1920
tgggtaaata gacagtggta taataataga tggaaatagc atacatcagt atgaaggaat   1980
gg                                                                  1982
```

<210> SEQ ID NO 5
<211> LENGTH: 875
<212> TYPE: PRT

-continued

<213> ORGANISM: HOMO SAPIENS
<220> FEATURE:
<223> OTHER INFORMATION: GI 3355606

<400> SEQUENCE: 5

```
Met Glu Arg Ala Gly Pro Ser Phe Gly Gln Gln Arg Gln Gln Gln Gln
 1               5                  10                  15
Pro Gln Gln Lys Gln Gln Arg Asp Gln Asp Ser Val Glu Ala
            20                  25                  30
Trp Leu Asp Asp His Trp Asp Phe Thr Phe Ser Tyr Phe Val Arg Lys
            35                  40                  45
Ala Thr Arg Glu Met Val Asn Ala Trp Phe Ala Glu Arg Val His Thr
 50                  55                  60
Ile Pro Val Cys Lys Glu Gly Ile Arg Gly His Thr Glu Ser Cys Ser
 65                  70                  75                  80
Cys Pro Leu Gln Gln Ser Pro Arg Ala Asp Asn Ser Val Pro Gly Thr
                85                  90                  95
Pro Thr Arg Lys Ile Ser Ala Ser Glu Phe Asp Arg Pro Leu Arg Pro
            100                 105                 110
Ile Val Val Lys Asp Ser Glu Gly Thr Val Ser Phe Leu Ser Asp Ser
            115                 120                 125
Glu Lys Lys Glu Gln Met Pro Leu Thr Pro Pro Arg Phe Asp His Asp
    130                 135                 140
Glu Gly Asp Gln Cys Ser Arg Leu Leu Glu Leu Val Lys Asp Ile Ser
145                 150                 155                 160
Ser His Leu Asp Val Thr Ala Leu Cys His Lys Ile Phe Leu His Ile
                165                 170                 175
His Gly Leu Ile Ser Ala Asp Arg Tyr Ser Leu Phe Leu Val Cys Glu
            180                 185                 190
Asp Ser Ser Asn Asp Lys Phe Leu Ile Ser Arg Leu Phe Asp Val Ala
            195                 200                 205
Glu Gly Ser Thr Leu Glu Glu Val Ser Asn Asn Cys Ile Arg Leu Glu
    210                 215                 220
Trp Asn Lys Gly Ile Val Gly His Val Ala Ala Leu Gly Glu Pro Leu
225                 230                 235                 240
Asn Ile Lys Asp Ala Tyr Glu Asp Pro Arg Phe Asn Ala Glu Val Asp
                245                 250                 255
Gln Ile Thr Gly Tyr Lys Thr Gln Ser Ile Leu Cys Met Pro Ile Lys
            260                 265                 270
Asn His Arg Glu Glu Val Val Gly Val Ala Gln Ala Ile Asn Lys Lys
    275                 280                 285
Ser Gly Asn Gly Gly Thr Phe Thr Glu Lys Asp Glu Lys Asp Phe Ala
    290                 295                 300
Ala Tyr Leu Ala Phe Cys Gly Ile Val Leu His Asn Ala Gln Leu Tyr
305                 310                 315                 320
Glu Thr Ser Leu Leu Glu Asn Lys Arg Asn Gln Val Leu Leu Asp Leu
                325                 330                 335
Ala Ser Leu Ile Phe Glu Glu Gln Gln Ser Leu Glu Val Ile Leu Lys
            340                 345                 350
Lys Ile Ala Ala Thr Ile Ile Ser Phe Met Gln Val Gln Lys Cys Thr
    355                 360                 365
Ile Phe Ile Val Asp Glu Asp Cys Ser Asp Ser Phe Ser Ser Val Phe
    370                 375                 380
```

```
-continued

His Met Glu Cys Glu Leu Glu Lys Ser Ser Asp Thr Leu Thr Arg
385                 390                 395                 400

Glu His Asp Ala Asn Lys Ile Asn Tyr Met Tyr Ala Gln Tyr Val Lys
            405                 410                 415

Asn Thr Met Glu Pro Leu Asn Ile Pro Asp Val Ser Lys Asp Lys Arg
        420                 425                 430

Phe Pro Trp Thr Thr Glu Asn Thr Gly Asn Val Asn Gln Gln Cys Ile
        435                 440                 445

Arg Ser Leu Leu Cys Thr Pro Ile Lys Asn Gly Lys Asn Lys Val
450                 455                 460

Ile Gly Val Cys Gln Leu Val Asn Lys Met Glu Glu Asn Thr Gly Lys
465                 470                 475                 480

Val Lys Pro Phe Asn Arg Asn Asp Glu Gln Phe Leu Glu Ala Phe Val
            485                 490                 495

Ile Phe Cys Gly Leu Gly Ile Gln Asn Thr Gln Met Tyr Glu Ala Val
            500                 505                 510

Glu Arg Ala Met Ala Lys Gln Met Val Thr Leu Glu Val Leu Ser Tyr
        515                 520                 525

His Ala Ser Ala Ala Glu Glu Thr Arg Glu Leu Gln Ser Leu Ala
        530                 535                 540

Ala Ala Val Val Pro Ser Ala Gln Thr Leu Lys Ile Thr Asp Phe Ser
545                 550                 555                 560

Phe Ser Asp Phe Glu Leu Ser Asp Leu Glu Thr Ala Leu Cys Thr Ile
            565                 570                 575

Arg Met Phe Thr Asp Leu Asn Leu Val Gln Asn Phe Gln Met Lys His
            580                 585                 590

Glu Val Leu Cys Arg Trp Ile Leu Ser Val Lys Lys Asn Tyr Arg Lys
        595                 600                 605

Asn Val Ala Tyr His Asn Trp Arg His Ala Phe Asn Thr Ala Gln Cys
            610                 615                 620

Met Phe Ala Ala Leu Lys Ala Gly Lys Ile Gln Asn Lys Leu Thr Asp
625                 630                 635                 640

Leu Glu Ile Leu Ala Leu Leu Ile Ala Ala Leu Ser His Asp Leu Asp
                645                 650                 655

His Arg Gly Val Asn Asn Ser Tyr Ile Gln Arg Ser Glu His Pro Leu
            660                 665                 670

Ala Gln Leu Tyr Cys His Ser Ile Met Glu His His Phe Asp Gln
        675                 680                 685

Cys Leu Met Ile Leu Asn Ser Pro Gly Asn Gln Ile Leu Ser Gly Leu
690                 695                 700

Ser Ile Glu Glu Tyr Lys Thr Thr Leu Lys Ile Ile Lys Gln Ala Ile
705                 710                 715                 720

Leu Ala Thr Asp Leu Ala Leu Tyr Ile Lys Arg Arg Gly Glu Phe Phe
            725                 730                 735

Glu Leu Ile Arg Lys Asn Gln Phe Asn Leu Glu Asp Pro His Gln Lys
            740                 745                 750

Glu Leu Phe Leu Ala Met Leu Met Thr Ala Cys Asp Leu Ser Ala Ile
            755                 760                 765

Thr Lys Pro Trp Pro Ile Gln Gln Arg Ile Ala Glu Leu Val Ala Thr
770                 775                 780

Glu Phe Phe Asp Gln Gly Asp Arg Glu Arg Lys Glu Leu Asn Ile Glu
785                 790                 795                 800
```

```
Pro Thr Asp Leu Met Asn Arg Glu Lys Lys Asn Lys Ile Pro Ser Met
                805                 810                 815

Gln Val Gly Phe Ile Asp Ala Ile Cys Leu Gln Leu Tyr Glu Ala Leu
                820                 825                 830

Thr His Val Ser Glu Asp Cys Phe Pro Leu Leu Asp Gly Cys Arg Lys
                835                 840                 845

Asn Arg Gln Lys Trp Gln Ala Leu Ala Glu Gln Gln Glu Lys Met Leu
        850                 855                 860

Ile Asn Gly Glu Ser Gly Gln Ala Lys Arg Asn
865                 870                 875

<210> SEQ ID NO 6
<211> LENGTH: 43
<212> TYPE: DNA
<213> ORGANISM: HOMO SAPIENS

<400> SEQUENCE: 6
ccaaatcccg gtccgagatg tccccaaagt gcagtgctga tgc                         43

<210> SEQ ID NO 7
<211> LENGTH: 41
<212> TYPE: DNA
<213> ORGANISM: HOMO SAPIENS

<400> SEQUENCE: 7
cgggtacctc gagttattag ttcctgtctt ccttggctac c                           41
```

HUMAN CYCLIC NUCLEOTIDE PDES

This application is a continuation-in-part of U.S. Ser. No. 09/226,741 filed Jan. 7, 1999, now U.S. Pat. No. 6,100,037.

FIELD OF THE INVENTION

This invention relates to nucleic acid and amino acid sequences of human cyclic nucleotide phosphodiesterases and their mammalian variants and to the use of these sequences in the diagnosis and treatment of cancer and immune disorders.

BACKGROUND OF THE INVENTION

Cyclic nucleotides (cAMP and cGMP) function as intracellular second messengers to transduce a variety of extracellular signals including hormones, light, and neurotransmitters. Cyclic nucleotide phosphodiesterases (PDEs) degrade cyclic nucleotides to the corresponding monophosphates, thereby regulating the intracellular concentrations of cyclic nucleotides and their effects on signal transduction. At least seven families of mammalian PDEs have been identified based on substrate specificity and affinity, sensitivity to cofactors, and sensitivity to inhibitory drugs (Beavo (1995) Physiol Rev 75:725–748). Several of these families contain distinct genes, many of which are expressed in different tissues as splice variants. Within families, there are multiple isozymes and multiple splice variants of those isozymes. The existence of multiple PDE families, isozymes, and splice variants presents an opportunity for regulation of cyclic nucleotide levels and functions.

Type 1 PDEs (PDE1s) are $Ca^{2+}$/calmodulin-dependent and appear to be encoded by three different genes, each having at least two different splice variants. PDE1s have been found in the lung, heart, and brain. Some of the $Ca^{2+}$/calmodulin-dependent PDEs are regulated in vitro by phosphorylation and dephosphorylation. Phosphorylation of PDE1 decreases the affinity of the enzyme for calmodulin, decreases PDE activity, and increases steady state levels of cAMP. PDE2s are cGMP stimulated PDEs that are localized in the brain and are thought to mediate the effects of cAMP on catecholamine secretion. PDE3s are one of the major families of PDEs present in vascular smooth muscle. PDE3s are inhibited by cGMP, have high specificity for cAMP as a substrate, and play a role in cardiac function. One isozyme of PDE3 is regulated by one or more insulin-dependent kinases. PDE4s are the predominant isoenzymes in most inflammatory cells, and some PDE4s are activated by cAMP-dependent phosphorylation. PDE5s are thought to be cGMP specific but may also hydrolyze cAMP. High levels of PDE5s are found in most smooth muscle preparations, in platelets, and in the kidney. PDE6s play a role in vision and are regulated by light and cGMP. The PDE7 class, consisting of only one known member, is cAMP-specific and is most closely related to PDE4. PDE7 is not inhibited by rolipram, a specific inhibitor of PDE4 (Beavo, supra). PDE8 and PDE9 represent two new families of PDEs. PDE8s are cAMP specific, most closely related to PDE4, insensitive to rolipram, and sensitive to dipyridimole. PDE9s are cGMP specific and sensitive only to the PDE inhibitor, zaprinast.

PDEs are composed of a catalytic domain of about 270 amino acids, an N-terminal regulatory domain responsible for binding cofactors, and, in some cases, a C-terminal domain of unknown function. A conserved motif, HDXXHXGXXN, has been identified in the catalytic domain of all PDEs. In PDE5, an N-terminal cGMP binding domain spans about 380 amino acid residues and comprises tandem repeats of the conserved sequence motif N(R/K) $XnFX_3DE$ (McAllister-Lucas et al. (1993) J Biol Chem 268:22863–22873). The NKXnD motif has been shown by mutagenesis to be important for cGMP binding (Turko et al. (1996) J Biol Chem 271:22240–22244). PDE families display approximately 30% amino acid identity within the catalytic domain; however, isozymes within the same family typically display about 85–95% identity in this region (e.g. PDE4A vs PDE4B). Furthermore, within a family there is extensive sequence similarity (>60%) outside the catalytic domain; while across families, there is little or no sequence similarity.

Many functions of immune and inflammatory responses are inhibited by agents that increase intracellular levels of cAMP (Verghese et al. (1995) Mol Pharmacol 47:1164–1171). A variety of diseases have been attributed to increased PDE activity and associated with decreased levels of cyclic nucleotides. A form of diabetes insipidus in the mouse has been associated with increased PDE4 activity, and an increase in low-$K_m$ cAMP PDE activity has been reported in leukocytes of atopic patients. Defects in PDEs have also been associated with retinal disease. Retinal degeneration in the rd mouse, autosomal recessive retinitis pigmentosa in humans, and rod/cone dysplasia 1 in Irish Setter dogs have been attributed to mutations in the PDE6B gene. PDE3 has been associated with cardiac disease.

Many inhibitors of PDEs have been identified and have undergone clinical evaluation. PDE3 inhibitors are being developed as antithrombotic agents, antihypertensive agents, and as cardiotonic agents useful in the treatment of congestive heart failure. Rolipram, a PDE4 inhibitor, has been used in the treatment of depression, and other inhibitors of PDE4 are undergoing evaluation as anti-inflammatory agents. Rolipram has also been shown to inhibit lipopolysaccharide induced TNF-α which has been shown to enhance HIV-1 replication in vitro. Therefore, rolipram may inhibit HIV-1 replication (Angel et al. (1995) AIDS 9:1137–44). Additionally, rolipram, based on its ability to suppress the production of cytokines, such as TNF-α and β and interferon γ, has been shown to be effective in the treatment of encephalomyelitis. Rolipram may also be effective in treating tardive dyskinesia and was effective in treating multiple sclerosis in an experimental animal model (Sommer et al. (1995) Nature Med 1:244–248; Sasaki et al. (1995) Eur J Pharmacol 282:71–76).

Theophylline is a nonspecific PDE inhibitor used in the treatment of bronchial asthma and other respiratory diseases. Theophylline is believed to act on airway smooth muscle function and in an anti-inflamatory or immunomodulatory capacity in the treatment of respiratory diseases (Banner and Page (1995) Eur Respir J 8:996–1000). Pentoxifylline is another nonspecific PDE inhibitor used in the treatment of intermittent claudication and diabetes-induced peripheral vascular disease. Pentoxifylline is also known to block TNF-α production and may inhibit HIV-1 replication (Angel, supra).

PDEs have also been reported to effect cellular proliferation of a variety of cell types and have been implicated in various cancers. Bang et al. (1994; Proc Natl Acad Sci 91:5330–5334) reported that growth of prostate carcinoma cell lines DU 145 and LNCaP was inhibited by delivery of cAMP derivatives and phosphodiesterase inhibitors. These cells also showed a permanent conversion in phenotype from epithelial to neuronal morphology. Others have suggested that PDE inhibitors have the potential to regulate mesangial cell proliferation and lymphocyte proliferation (Matousovic et al. (1995) J Clin Invest 96:401–410; Joulain et al. (1995) J Lipid Mediat Cell Signal 11:63–79, respectively). Finally, Deonarain et al.(1994; Br J Cancer 70:786–94) describe a cancer treatment that involves intracellular delivery of phosphodiesterases to particular cellular compartments of tumors which results in cell death.

The discovery of a new human cyclic nucleotide phosphodiesterase and the polynucleotides encoding them satisfies a need in the art by providing new compositions which are useful in the diagnosis and treatment of cancer and immune disorders.

SUMMARY OF THE INVENTION

The invention is based on the discovery of new human cyclic nucleotide phosphodiesterases referred to collectively as "HSPDE10A" and individually as "HSPDE10A " and "HSPDE10A2", the polynucleotides encoding HSPDE10A1 and HSPDE10A2, and the use of these compositions for the diagnosis and treatment of cancer and immune disorders.

The invention features a purified protein comprising the amino acid sequence of SEQ ID NO:1, SEQ ID NO:3, or portions thereof. The invention provides a purified variant having at least 90% amino acid sequence identity to the amino acid sequence of SEQ ID NO:1, SEQ ID NO:3, or portions thereof.

The invention provides an isolated polynucleotide encoding the protein comprising the amino acid sequence of SEQ ID NO:1, SEQ ID NO:3, or portions thereof. The invention also provides an isolated polynucleotide which hybridizes under stringent conditions to the polynucleotide encoding the protein comprising the amino acid sequence of SEQ ID NO:1, SEQ ID NO:3, or portions thereof. The invention further provides an isolated polynucleotide having a sequence which is complementary to the polynucleotide encoding the protein comprising the amino acid sequence of SEQ ID NO:1, SEQ ID NO:3, or portions thereof.

The invention provides an isolated polynucleotide comprising the nucleic acid sequence of SEQ ID NO:2, SEQ ID NO:4, or fragments thereof and isolated variants having at least 70% polynucleotide sequence identity to the polynucleotide comprising the polynucleotide sequence of SEQ ID NO:2, SEQ ID NO:4, or fragments thereof. The invention also provides an isolated polynucleotide having a sequence complementary to the polynucleotide comprising the polynucleotide sequence of SEQ ID NO:2, SEQ ID NO:4, or fragments thereof.

The invention provides a method for detecting a polynucleotide in a sample containing nucleic acids comprising hybridizing the complement of the polynucleotide to at least one of the nucleic acid of the sample, thereby forming a hybridization complex, and detecting the hybridization complex, wherein the presence of the hybridization complex indicates the presence of the polynucleotide in the sample. In one aspect, the method further comprises amplifying the nucleic acids of the sample prior to hybridization.

The invention also provides an expression vector containing the polynucleotide encoding the protein comprising the amino acid sequence of SEQ ID NO:1 or SEQ ID NO:3. In one aspect, the expression vector is contained within a host cell. The invention further provides a method for using a polynucleotide to produce a protein comprising culturing the host cell under conditions for expression of the protein and recovering the protein from the culture. The invention further provides a composition comprising a purified protein having the amino acid sequence of SEQ ID NO:1, SEQ ID NO:3, or portions thereof in conjunction with a pharmaceutical carrier. The invention also provides a method of using the protein to screen a plurality of molecules or compounds to identify a ligand comprising combining the protein with the molecules or compounds under conditions to allow specific binding and detecting specific binding, thereby identifying a ligand which specifically binds the protein. In one aspect, the molecules and compounds are selected from the group consisting of DNA molecules, RNA molecules, peptide nucleic acid molecules, peptides, proteins, agonists, antagonists, inhibitors, drug compounds and pharmaceutical agents. The invention further provides a composition comprising a purified agonist which specifically binds the protein having the amino acid sequence of SEQ ID NO:1, SEQ ID NO:3, or portions thereof.

The invention provides methods for using the protein to produce polyclonal or monoclonal antibodies which specifically bind the protein. The invention also provides a purified antibody which specifically binds to a protein comprising the amino acid sequence of SEQ ID NO:1 or SEQ ID NO:3. The invention further provides a method for using the antibody in an assay for adenofibromatous hyperplasia of the prostate comprising contacting the antibody with a sample from a patient, detecting complex formation between the antibody and protein, comparing complex formation with a standard, wherein the difference in complex formation indicates the presence of the disease.

The invention provides a method for treating adenofibromatous hyperplasia of the prostate as it is associated with decreased expression or activity of HSPDE10A comprising administering to a subject in need of such treatment a composition comprising a purified protein having the amino acid sequence of SEQ ID NO:1, SEQ ID NO:3, or portions thereof, in conjunction with a pharmaceutical carrier. The invention also provides a method for treating adenofibromatous hyperplasia of the prostate comprising administering to a subject in need of such treatment a composition comprising an agonist which specifically binds the protein having the amino acid sequence of SEQ ID NO:1, SEQ ID NO:3, or portions thereof The invention also provides a method for treating a disorder associated with increased expression or activity of HSPDE10A, the method comprising administering to a subject in need of such treatment an antagonist of the protein having the amino acid sequence of SEQ ID NO:1, SEQ ID NO:3, or portions thereof.

BRIEF DESCRIPTION OF THE FIGURES AND TABLE

FIGS. 1A, 1B, 1C, 1D, and 1E show the amino acid sequence (SEQ ID NO:1) and nucleic acid sequence (SEQ ID NO:2) of HSPDE10A1. The alignment was produced using MACDNASIS PRO software (Hitachi Software Engineering, South San Francisco, Calif.).

FIGS. 2A, 2B, 2C, 2D, 2E, and 2F show the amino acid sequence (SEQ ID NO:3) and nucleic acid sequence (SEQ ID NO:4) of HSPDE10A2. The alignment was produced using MACDNASIS PRO software.

FIGS. 3A, 3B, 3C, 3D, and 3E show the amino acid sequence alignments between HSPDE10A1 (SEQ ID NO:1), HSPDE10A2 (SEQ ID NO:3), and human PDE5, HPDE5A1 (g3355606; SEQ ID NO:5), produced using the MEGALIGN program (DNASTAR, Madison, Wis.).

Figure 4B:
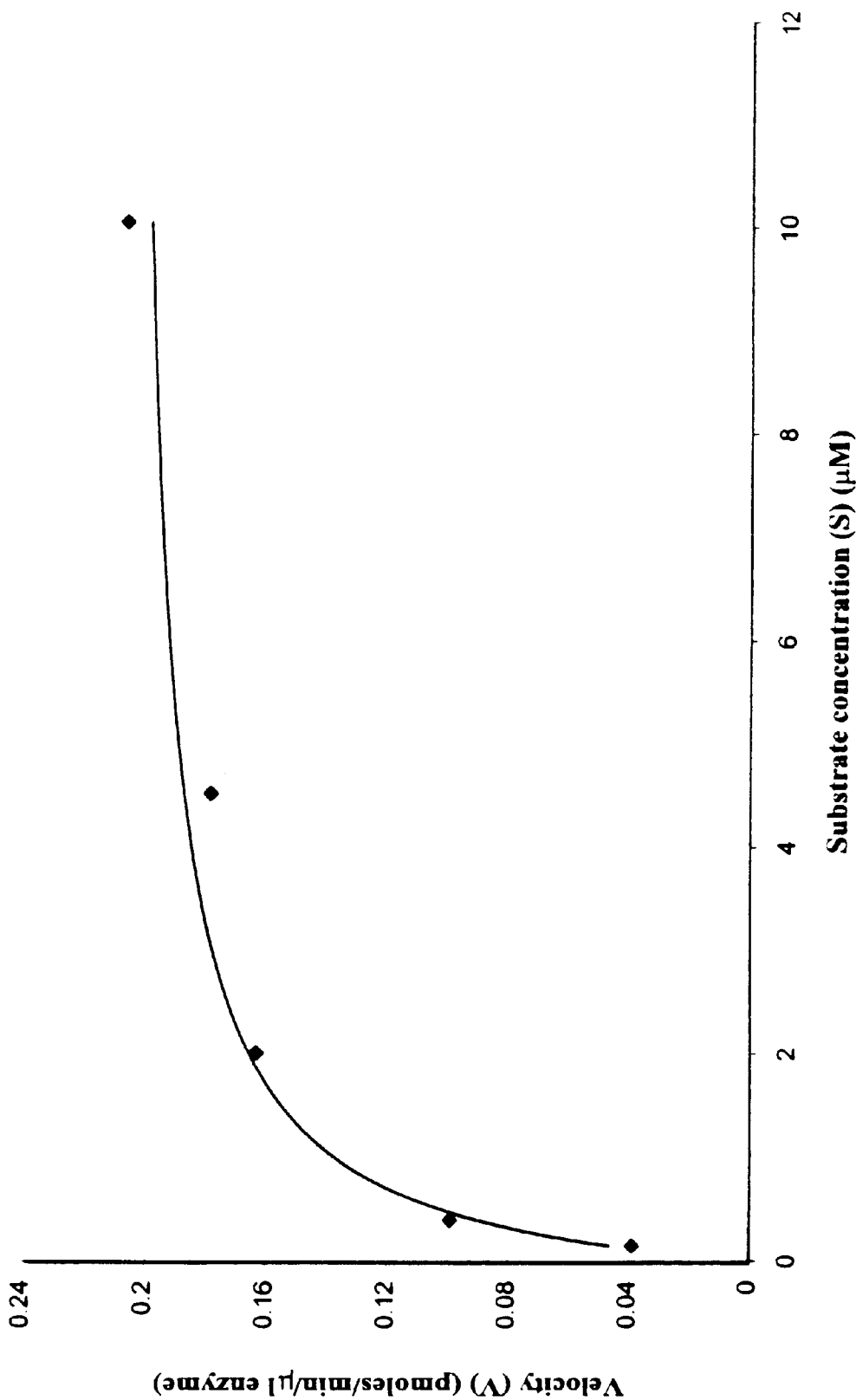

FIGS. 4A and 4B show the activity assay for HSPDE10A1 using cAMP and cGMP as substrates, respectively. The positive X axis represents the substrate concentration (mM), and the positive Y axis represents the reaction velocity in pmoles/minute/ml enzyme. $K_m$ and $V_{max}$ values for the enzyme activity with each substrate were calculated from a Michaelis-Menten plot using the "Fit Curve" Microsoft Excel extension program.

Figure 5A:
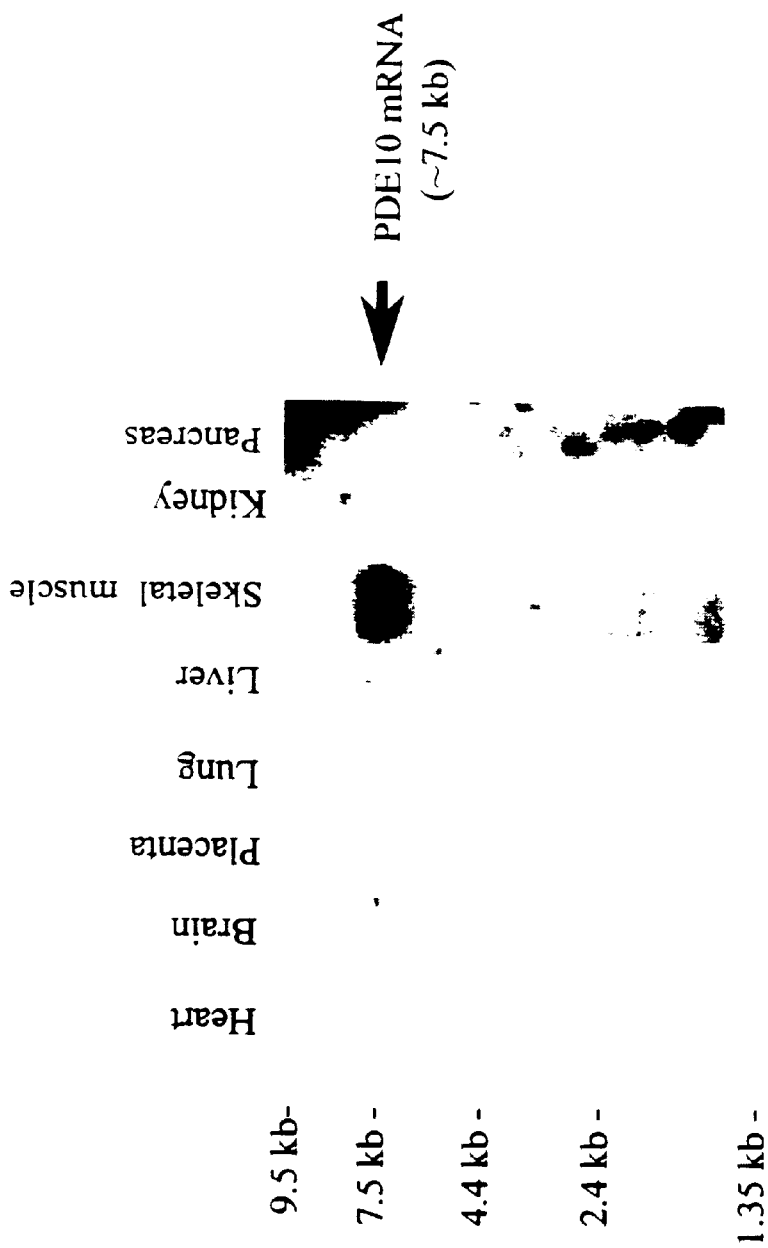
Figure 5B:
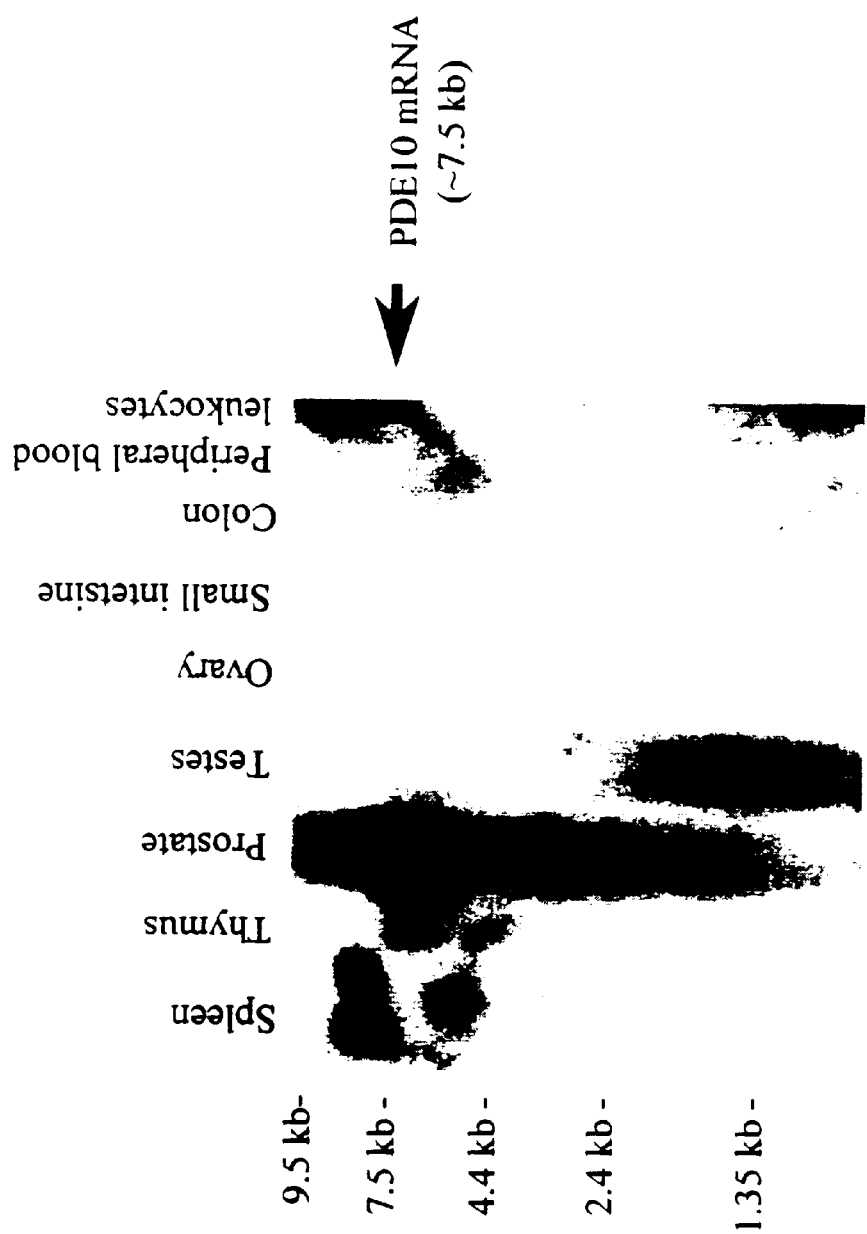

FIGS. 5A and 5B show the membrane-based northern analysis of HSPDE10A expression in human tissues. The X axis presents the various tissues analyzed, and the Y axis presents various size markers. The arrow indicates the location of the major (~7.5 kb) transcript of HSPDE10A.

Figure 6:
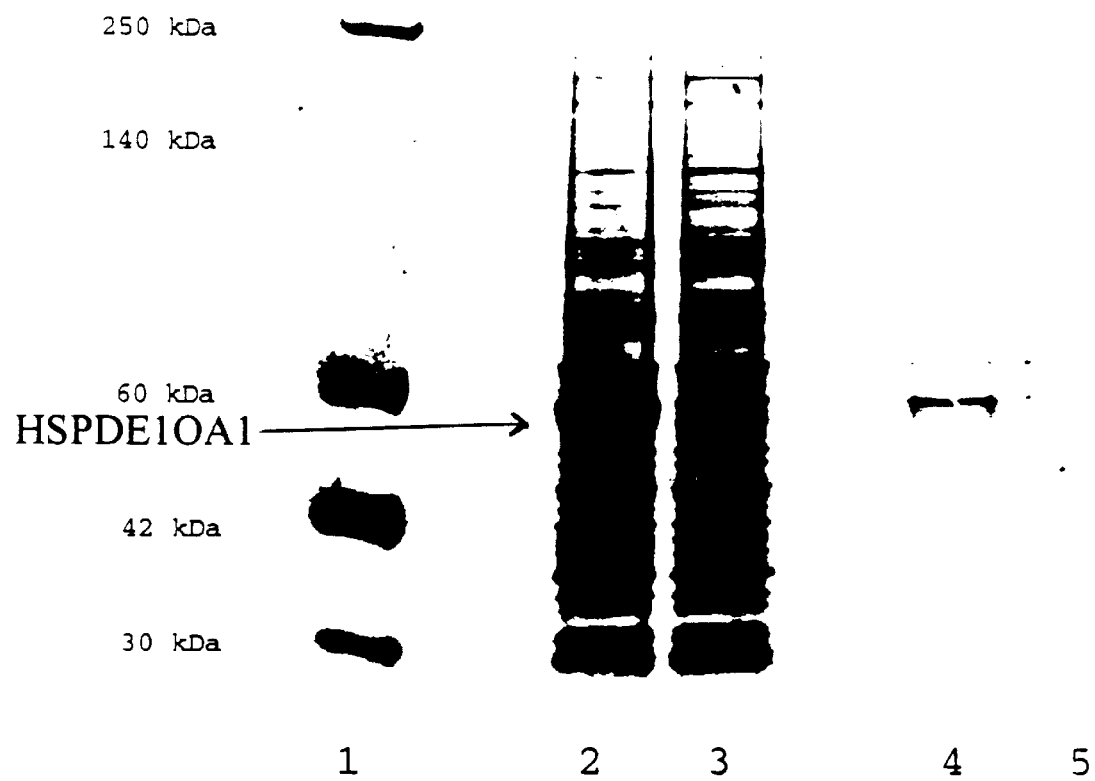

FIG. 6 shows the expression of full length HSPDE10A1 in Sf9 cells (arrow; predicted molecular weight ~56 kDa). Lane 1 shows various size markers and their molecular weights. Lanes 2 and 4, infected cells at 64,000 and 12,800 cell equivalents, respectively, show HSPDE10A1. Lanes 3 and 5, mock-infected cells at 64,000 and 12,800 cell equivalents, respectively, fail to show the presence of HSPDE10A1.

FIG. 7 shows the northern analysis for HSPDE10A1 produced using the LIFESEQ Gold database (Incyte Genomics, Palo Alto, Calif.). In the first range, the first column presents the tissue categories; the second column, the number of clones in the tissue category; the third column, the number of libraries in which at least one transcript was found; the fourth column, absolute abundance of the transcript; and the fifth column, percent abundance of the trancript. In the second range, the first column lists the library name, the second column, the number of clones sequenced for that library; the third column, description of the tissue; the fourth column, absolute abundance of the transcript; and the fifth column, percent abundance of the trancript.

Table 1 shows the effects of various PDE inhibitors on the activity of HSPDE10A1. Assays were carried out using cGMP as a substrate at a concentration of 0.17 mM, equal to ~⅓ of the $K_m$ of cGMP. Inhibitors were tested over a range of concentrations from ~0.5 to ~110 mM. $IC_{50}$ (or $K_i$) values were extrapolated from the dose response curves.

Table 2 shows the programs, their descriptions, references, and threshold parameters used to analyze HSPDE10A.

DESCRIPTION OF THE INVENTION

Before the present proteins, polynucleotides, and methods are described, it is understood that this invention is not limited to the particular machines, materials and methods described as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. For example, a reference to "a host cell" includes a plurality of such host cells, and a reference to "an antibody" is a reference to one or more antibodies and equivalents thereof known to those of skill in the art.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All patents and publications mentioned herein are hereby incorporated by reference and have been cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"HSPDE10A" refers to the amino acid sequences of a purified HSPDE10A obtained from any species including bovine, ovine, porcine, murine, equine, rodent, and preferably the human species, from any source, whether natural, synthetic, semi-synthetic, or recombinant.

"Array" refers to an ordered arrangement of at least two polynucleotides on a substrate. The arrangement of from about two to about 40,000 polynucleotides on the substrate assures that the size and signal intensity of each labeled hybridization complex formed between a polynucleotide and a sample nucleic acid is individually distinguishable.

The "complement" of a polynucleotide of the Sequence Listing refers to a nucleic acid molecule which is completely complementary over its full length and which will hybridize to the polynucleotide or an mRNA under conditions of high stringency.

"Polynucleotide" refers to an isolated cDNA, nucleic acid molecule, or any fragment or complement thereof. It may have originated recombinantly or synthetically, be double-stranded or single-stranded, represent coding and/or non-coding sequence, an exon with or without an intron from a genomic DNA molecule.

The phrase "polynucleotide encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al. (1990) J Mol Biol 215:403–410) which provides identity within the conserved region. Brenner et al. (1998; Proc Natl Acad Sci 95:6073–6078) who analyzed BLAST for its ability to identify structural homologs by sequence identity found 30% identity is a reliable threshold for sequence alignments of at least 150 residues and 40% is a reasonable threshold for alignments of at least 70 residues (Brenner et al., p. 6076, column 2).

"Derivative" refers to a polynucleotide or a protein that has been subjected to a chemical modification. Derivatization of a polynucleotide can involve substitution of a non-traditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by the absence, presence, or at least two-fold changes in the amount of transcribed messenger RNA or translated protein in a sample.

"Disorder" refers to conditions, diseases or syndromes in which the polynucleotides and HSPDE10A are differentially expressed such as adenofibromatous hyperplasia of the prostate.

"Fragment" refers to a chain of consecutive nucleotides from about 61 to about 5000 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription or translation.

A "hybridization complex" is formed between a polynucleotide and a nucleic acid of a sample when the purines of one molecule hydrogen bond with the pyrimidines of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a cDNA molecule or polynucleotide, or to an epitope or a protein. Such ligands stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleotides in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a polynucleotide that hybridizes to at least one nucleic acid in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as a Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which polynucleotides or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a polynucleotide or a protein encoded by the polynucleotide. Splice variants may be determined by BLAST score, wherein the score is at least 100, and preferably at least 400. Allelic variants have a high percent identity to the polynucleotides and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid

THE INVENTION

The invention is based on the discovery of new human cyclic nucleotide phosphodiesterases (HSPDE10A), the polynucleotides encoding HSPDE10A, and the use of these compositions for the diagnosis and treatment of cancer and immune disorders.

Nucleic acids encoding the HSPDE10A of the present invention were identified in Incyte Clone 826776 from the prostate cDNA library (PROSTUT04) using BLAST analysis and human PDE5 (GI 3355606) as a query sequence against the LIFESEQ database (Incyte Genomics, Palo Alto, Calif.). Full length cDNA sequences of HSPDE10A were obtained from a human skeletal muscle library using the complete cDNA insert of Incyte Clone 826776 as a hybridization probe. Clone 826776 has identity with the nucleotide sequence encoding HSPDE10A from nucleotide 627 to nucleotide 888. The oligonucleotide of SEQ ID NO:2 from about nucleotide 1168 to about nucleotide 1212 is useful in hybridization or amplification technologies to identify SEQ ID NO:2 and to distinguish between SEQ ID NO:2 and a related sequence. The oligonucleotide of SEQ ID NO:4 from about nucleotide 1183 to about nucleotide 1227 is useful in hybridization or amplification technologies to identify SEQ ID NO:4 and to distinguish between SEQ ID NO:4 and a related sequence. FIG. 7 shows the electronic northern analysis for HSPDE10A.

In one embodiment, the invention encompasses a protein comprising the amino acid sequence of SEQ ID NO:1, as shown in FIGS. 1A–1E. HSPDE10A1 is 490 amino acids in length and has a putative cGMP binding motif in the sequence $N_{88}$RLDGKPFDDAD of SEQ ID NO:1 and a PDE signature motif at $H_{260}$DLDHRGTNN of SEQ ID NO:1. As shown in FIGS. 3A–3E, HSPDE10A1 has chemical and structural similarity with human PDE5, HSPDE5A1 (g3355606; SEQ ID NO:5). In particular, HSPDE10A1 and HSPDE5A1 share 42% identity. The ~270 amino acid catalytic domain found in all PDEs extends between residues $F_{196}$ and $R_{458}$ in HSPDE10A1 and is 50% identical to HSPDE5A1 in this region. The putative cGMP binding motif in HSPDE10A1 beginning at residue $N_{88}$ is coincident with the tandem repeat motif for cGMP binding in HSPDE5A1 beginning at residue $N_{472}$, and the PDE signature sequence for HSPDE10A1 beginning at residue $H_{260}$ is conserved in HSPDE5A as well. HSPDE10A1 shares a slightly lesser degree of homology, ranging from 25% to 44%, with other representatives of PDE families 1, 2, 3, 4, 6, 7, 8, and 9 (data not shown). Portions of HSPDE10A which are hydrophillic and appropriate to use as antigenic epitopes include residues 10–25, 45–60, 88–103, 145–158, and 260–275. Antibodies produced epitopes comprising residues 350–365 and 396–411 would distinguish HSPDE10A1 from HSPDE10A2. These epitopes are synthesized, coupled to KLH and used to produce antibodies which bind specifically to HSPDE10A and are diagnostics for examining biopsied prostate tissues potentially affected by adenofibromatous hyperplasia.

In another embodiment, the invention encompasses a protein comprising the amino acid sequence of SEQ ID NO:3. As shown in FIGS. 2A–2E, HSPDE10A2 is 367 amino acids in length and also contains the putative cGMP binding motif at $N_{88}$RLDGKPFDDAD of SEQ ID NO:3 and a PDE signature motif at $H_{260}$DLDHRGTNN of SEQ ID NO:3. As shown in FIGS. 3A–3E, HSPDE10A2 is identical to HSPDE10A1 between residues $M_1$ and $E_{338}$, but differs in the C-terminal portion of the molecule from $E_{339}$ to Y367. HSPDE10A2 also shares 40% identity with HSPDE5A1.

A cDNA construct encoding the full length amino acid sequence of HSPDE10A1 was cloned into the baculovirus transfer vector pFASTBAC, expressed in Sf9 cells, and the enzyme partially purified from these cells for enzyme assays. FIGS. 4A and 4B show the kinetics of HSPDE10A1 enzyme activity with cAMP (FIG. 4A) and cGMP (FIG. 4B) as substrates. Both substrates are hydrolyzed at a similar rate ($V_{max}$=0.23 and 0.21 μmole/min/ml enzyme for cAMP and cGMP, respectively), and with a similar affinity for HSPDE10A1 ($K_m$=1.04 and 0.52 μM for cAMP and cGMP, respectively). The data confirms that HSPDE10A1 is a PDE capable of hydrolyzing both cAMP and cGMP at physiologically relevant concentrations. The effects of various known PDE inhibitors on the activity of HSPDE10A1 using cGMP as a substrate are shown in Table 1. HSPDE10A1 was relatively insensitive to both milrinone and rolipram, which are selective for PDE3 and PDE4 respectively, with $IC_{50}$ values of >200 μM and 160 μM, respectively. The nonselective PDE inhibitor IBMX (3-isobutyl1-methylxanthine) inhibited HSPDE10A1 with an $IC_{50}$ of 40 μM, which is within the range observed for other PDEs, except the IBMX-insensitive PDE8. The so-called cGMP PDE-specific inhibitor zaprinast, which is selective for PDE5 and PDE6, was moderately effectivet against HSPDE10A1 with an $IC_{50}$ of 8 μM (10–40 fold higher than PDEs 5 and 6).

The degree of similarity exhibited between the HSPDE10A1 and representatives of the other families of PDEs in the catalytic domain (25% to 50%) is consistent with that demonstrated between different PDE families (~30%). HSPDE10A1 is further distinguished from other known families by its dual specificity for both cAMP and cGMP and by its pattern of inhibition by known PDE inhibitors. HSPDE10A1 therefore appears to be a member of a new family of cyclic nucleotide phosphodiesterases designated PDE10.

Membrane-based northern analysis (FIGS. 5A–5B) shows the expression of HSPDE10A as a major transcript of ~7.5 kb in skeletal muscle and prostate tissue. An additional ~3.0 kb mRNA was detected in prostate alone; a less prominent transcript of ~1.5 kb occurs in skeletal muscle and testes. These data suggest the existence of at least three HSPDE10A splice variants. Electronic northern analysis using the LIFESEQ database (Incyte Genomics) further shows the expression of HSPDE10A in cancerous prostate tissue.

FIG. 6 shows the expression of HSPDE10A1 in cell lysates of Sf9 cells transformed with a baculovirus vector containing an untagged cDNA construct. An ~56 kDa protein was detected by Coomassie blue staining (native HSPDE10A1; FIG. 6) and by western immunoblotting of a FLAG-tagged HSPDE10A1 using an anti-FLAG antibody (data not shown).

The invention also encompasses polynucleotides which encode HSPDE10A. In a particular embodiment, the invention encompasses a polynucleotide comprising the nucleic acid sequence of SEQ ID NO:2 which encodes HSPDE10A1. In another embodiment, the invention encompasses a polynucleotide comprising the nucleic acid sequence of SEQ ID NO:4 which encodes HSPDE10A2.

It will be appreciated by those skilled in the art that as a result of the degeneracy of the genetic code, a multitude of polynucleotide sequences encoding HSPDE10A, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HSPDE10A, and all such variations are to be considered as being specifically disclosed.

Although nucleotide sequences which encode HSPDE10A and its variants are preferably capable of hybridizing to the nucleotide sequence of the naturally occurring HSPDE10A under appropriately selected conditions of stringency, it may be advantageous to produce nucleotide sequences encoding HSPDE10A or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSPDE10A and its derivatives without altering the encoded amino acid sequences include the production of RNA transcripts having more desirable properties, such as a greater half-life, than transcripts produced from the naturally occurring sequence.

The invention also encompasses production of DNA sequences which encode HSPDE10A and HSPDE10A derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HSPDE10A.

Also encompassed by the invention are polynucleotide sequences that are capable of hybridizing to the claimed polynucleotide sequences, and, in particular, to those shown in SEQ ID NO:2, or to a fragment of SEQ ID NO:2, under various conditions of stringency (Wahl and Berger (1987) Methods Enzymol 152:399–407; Kimmel (1987) Methods Enzymol 152:507–511). For example, stringent salt concentration will ordinarily be less than about 750 mM NaCl and 75 mM trisodium citrate (SSC), preferably less than about 500 mM NaCl and 50 mM SSC, and most preferably less than about 250 mM NaCl and 25 mM SSC. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM SSC, and 1% SDS. In a more preferred embodiment, hybridization will occur at 37° C. in 500 mM NaCl, 50 mM SSC, 1% SDS, 35% formamide, and 100 $\mu$g/ml denatured salmon sperm DNA (ssDNA). In a most preferred embodiment, hybridization will occur at 42° C. in 250 mM NaCl, 25 mM SSC, 1% SDS, 50% formamide, and 200 $\mu$g/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM SSC, and most preferably less than about 15 mM NaCl and 1.5 mM SSC. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM SSC, and 0.1% SDS. In a more preferred embodiment, wash steps will occur at 42° C. in 15 mM NaCl, 1.5 mM SSC, and 0.1% SDS. In a most preferred embodiment, wash steps will occur at 68° C. in 15 mM NaCl, 1.5 mM SSC, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE, Taq polymerase, thermostable T7 polymerase (Amersham Pharmacia Biotech (APB), Piscataway, N.J.), or combinations of polymerases and proofreading exonucleases such as those found in the ELONGASE amplification system (Life Technologies, Gaithersburg, Md.). Preferably, sequence preparation is automated with machines such as the Robbins Hydra microdispenser (Robbins Scientific, Sunnyvale, Calif.), MICROLAB 2200 system (Hamilton, Reno, Nev.), DNA ENGINE thermal cycler (MJ Research, Watertown, Mass.) and the ABI CATALYST 800 thermal cycler (PE Biosystems). Sequencing is then carried out using either ABI 373 or 377 DNA sequencing systems (PE Biosystems) or the MEGABACE 1000 DNA sequencing system (APB). The resulting sequences are analyzed using a variety of algorithms which are well known in the art and reviewed in Ausubel (1997; Short Protocols in Molecular Biology, John Wiley & Sons, New York, N.Y., unit 7.7) and in Meyers (1995; Molecular Biology and Biotechnology, Wiley VCH, New York, N.Y., pp. 856–853).

The nucleic acid sequences encoding HSPDE10A may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar (1993) PCR Methods Applic 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia et al. (1988) Nucleic Acids Res 16:8186.) A third method, capture PCR, involves PCR amplification of DNA fragments adjacent to known sequences in human and yeast artificial chromosome DNA. (See, e.g., Lagerstrom et al. (1991) PCR Methods Applic 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker et al. (1991) Nucleic Acids Res 19:3055–306). Additionally, one may use PCR, nested primers, and PROMOTERFINDER libraries (Clontech, Palo Alto, Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth, Minn.) or another appropriate program, to be about 22 to 30 nucleotides in length, to have a GC content of about 50% or more, and to anneal to the template at temperatures of about 68° C. to 72° C. When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using GENOTYPER or SEQUENCE NAVIGATOR software (PE Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HSPDE10A may be cloned in recombinant DNA molecules that direct expression of HSPDE10A, or fragments or functional equivalents thereof, in appropriate host cells. Due to the inherent degeneracy of the genetic code, other DNA sequences which encode substantially the same or a functionally equivalent amino acid sequence may be produced and used to express HSPDE10A.

The nucleotide sequences of the present invention can be engineered using methods generally known in the art in order to alter HSPDE10A-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HSPDE10A may be synthesized, in whole or in part, using chemical methods well known in the art and described by Caruthers et al. (1980; Nucleic Acids Symp Ser (7) 215–223) and Horn et al. (1980; Nucleic Acids Symp Ser (7) 225–232). Alternatively, HSPDE10A itself or a fragment thereof may be synthesized using chemical methods. For example, peptide synthesis can be performed using various solid-phase techniques (Roberge et al. (1995) Science 269:202–204). Automated synthesis may be achieved using the ABI 431A peptide synthesizer (PE Biosystems). Additionally, the amino acid sequence of HSPDE10A, or any part thereof, may be altered during direct synthesis and/or combined with sequences from other proteins, or any part thereof, to produce a variant protein.

The peptide may be substantially purified by preparative high performance liquid chromatography. (Chiez and Regnier (1990) Methods Enzymol 182:392–421). The composition of the synthetic peptides may be confirmed by amino acid analysis or by sequencing. (See, e.g., Creighton (1984) *Proteins, Structures and Molecular Properties*, W H Freeman, New York, N.Y.)

In order to express a biologically active HSPDE10A, the nucleotide sequences encoding HSPDE10A or derivatives thereof may be inserted into an appropriate expression vector, i.e., a vector which contains the necessary elements for transcriptional and translational control of the inserted coding sequence in a host. These elements include regulatory sequences, such as enhancers, constitutive and inducible promoters, and 5' and 3' untranslated regions in the vector and in polynucleotide sequences encoding HSPDE10A. Such elements may vary in their strength and specificity. Specific initiation signals may also be used to achieve more efficient translation of sequences encoding HSPDE10A. Such signals include the ATG initiation codon and adjacent sequences, e.g. the Kozak sequence. In cases where sequences encoding HSPDE10A and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used (Scharf et al. (1994) Results Probl Cell Differ 20:125–162).

Methods which are well known to those skilled in the art may be used to construct expression vectors containing sequences encoding HSPDE10A and appropriate transcriptional and translational control elements. These methods include in vitro recombinant DNA techniques, synthetic techniques, and in vivo genetic recombination as described in Sambrook et al. (1989; *Molecular Cloning, A Laboratory Manual*, Cold Spring Harbor Press, Plainview, N.Y., ch. 4, 8, and 16–17) or in Ausubel et al. (1995; *Current Protocols in Molecular Biology*, John Wiley & Sons, New York, N.Y., ch. 9, 13, and 16).

A variety of expression vector/host systems may be utilized to contain and express sequences encoding HSPDE10A. These include, but are not limited to, microorganisms such as bacteria transformed with recombinant bacteriophage, plasmid, or cosmid DNA expression vectors; yeast transformed with yeast expression vectors; insect cell systems infected with baculovirus expression vectors; plant cell systems transformed with viral expression vectors (cauliflower mosaic virus, CaMV, or tobacco mosaic virus, TMV) or with bacterial expression vectors (Ti or pBR322 plasmids); or animal cell systems. The invention is not limited by the host cell employed.

In bacterial systems, a number of cloning and expression vectors may be selected depending upon the use intended for polynucleotide sequences encoding HSPDE10A. For example, routine cloning, subcloning, and propagation of polynucleotide sequences encoding HSPDE10A can be achieved using a multifunctional *E. coli* vector such as PBLUESCRIPT (Stratagene, La Jolla Calif.) or PSPORT1 plasmid (Life Technologies). Ligation of sequences encoding HSPDE10A into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence (Van Heeke and Schuster (1989) J Biol Chem 264:5503–5509). When large quantities of protein are needed for the production of antibodies, vectors containing the strong, inducible T5 or T7 bacteriophage promoter which direct high level expression of may be used.

Yeast expression systems may be used for production of HSPDE10A. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel (1995) supra; Grant et al. (1987) Methods Enzymol 153:516–54; and Scorer et al. (1994) Biotechnol 12:181–184.)

Plant systems may also be used for expression of HSPDE10A. Transcription of sequences encoding HSPDE10A may be driven by viral promoters such as the 35S and 19S promoters of CaMV used alone or in combination with the omega leader sequence from TMV (Takamatsu (1987) EMBO J 6:307–311). Alternatively, plant promoters such as the small subunit of RUBISCO or heat shock promoters may be used (Coruzzi et al. (1984) EMBO J 3:1671–1680; Broglie et al. (1984) Science 224:838–843; and Winter et al. (1991) Results Probl Cell Differ 17:85–105). These constructs can be introduced into plant cells by direct DNA or pathogen-mediated transformation (*The McGraw Hill Yearbook of Science and Technology* (1992) McGraw Hill, New York, N.Y., pp. 191–196).

In mammalian cells, a number of viral-based expression systems may be utilized. In cases where an adenovirus is used as an expression vector, sequences encoding HSPDE10A may be ligated into an adenovirus transcription/translation complex consisting of the late promoter and tripartite leader sequence. Insertion in a non-essential E1 or E3 region of the viral genome may be used to obtain infective virus which expresses HSPDE10A in host cells (Logan and Shenk (1984) Proc Natl Acad Sci 81:3655–3659). In addition, transcription enhancers, such as the RSV enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes (Harrington et al. (1997) Nature Genet 15:345–355).

For long term production of recombinant proteins in mammalian systems, stable expression of HSPDE10A in cell lines is preferred. For example, sequences encoding HSPDE10A can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻cells, respectively (Wigler et al. (1977) Cell 11:223–232; Lowy et al. (1980) Cell 22:817–823). Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively (Wigler et al. (1980) Proc Natl Acad Sci 77:3567–3570; Colbere-Garapin et al. (1981) J Mol Biol 150:1–14). Additional selectable genes have been described, trpB and hisD, which alter cellular requirements for metabolites (Hartman and Mulligan (1988) Proc Natl Acad Sci 85:8047–8051). Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable expression attributable to a specific vector system (Rhodes (1995) Methods Mol Biol 55:121–131).

Although the presence/absence of marker gene expression suggests that the gene of interest is also present, the presence and expression of the gene may need to be confirmed. For example, if the sequence encoding HSPDE10A is inserted within a marker gene sequence, transformed cells containing sequences encoding HSPDE10A can be identified by the absence of marker gene function. Alternatively, a marker gene can be placed in tandem with a sequence encoding HSPDE10A under the control of a single promoter. Expression of the marker gene in response to induction or selection usually indicates expression of the tandem gene as well.

In general, host cells that contain the nucleic acid sequence encoding HSPDE10A and that express HSPDE10A may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid sequences.

Immunological methods for detecting and measuring the expression of HSPDE10A using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HSPDE10A is preferred, but a competitive binding assay may be employed. These and other assays are well known in the art (Hampton et al. (1990) *Serological Methods, a Laboratory Manual*, APS Press, St Paul, Minn., Sect. IV; Coligan et al. (1997) *Current Protocols in Immunology*, Greene Pub. Associates and Wiley-Interscience, New York, N.Y.; and Pound (1998) *Immunochemical Protocols*, Humana Press, Totowa, N.J.).

A wide variety of labels and conjugation techniques are known by those skilled in the art and may be used in various nucleic acid and amino acid assays. Means for producing labeled hybridization or PCR probes for detecting sequences related to polynucleotides encoding HSPDE10A include oligolabeling, nick translation, end-labeling, or PCR amplification using a labeled nucleotide. Alternatively, the sequences encoding HSPDE10A, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by APB and Promega (Madison, Wis.). Reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HSPDE10A may be cultured under conditions for the expression and recovery of the protein from cell culture. The protein produced by a transformed cell may be secreted or retained intracellularly depending on the sequence and/or the vector used. As will be understood by those of skill in the art, expression vectors containing polynucleotides which encode HSPDE10A may be designed to contain signal sequences which direct secretion of HSPDE10A through a prokaryotic or eukaryotic cell membrane.

In addition, a host cell strain may be chosen for its ability to modulate expression of the inserted sequences or to process the expressed protein in the desired fashion. Such modifications of the protein include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (CHO, HeLa, MDCK, HEK293, WI38 and the like) are available from the ATCC (Manassas, Va.) and may be chosen to ensure the correct modification and processing of the recombinant protein.

In another embodiment of the invention, natural, modified, or recombinant nucleic acid sequences encoding HSPDE10A may be ligated to a heterologous sequence resulting in translation of a fusion protein in any of the aforementioned host systems. For example, a chimeric HSPDE10A protein containing a heterologous moiety that can be recognized by a commercially available antibody may facilitate the screening of peptide libraries for inhibitors of HSPDE10A activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HSPDE10A encoding sequence and the heterologous protein sequence, so that HSPDE10A may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled HSPDE10A may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HSPDE10A may be produced not only by recombinant production, but also by direct peptide synthesis using solid-phase techniques (Creighton, supra, pp. 55–60). Protein synthesis may be performed by manual techniques or by automation. Automated synthesis may be achieved, for example, using the ABI 431A peptide synthesizer (PE Biosystems). Various fragments of HSPDE10A may be synthesized separately and then combined to produce the full length molecule.

THERAPEUTICS

Chemical and structural similarity in the context of sequences and motifs exists between regions of HSPDE10A and human cyclic nucleotide phosphodiesterases. In addition, the expression of HSPDE10A is closely associated with normal skeletal muscle and prostate tissues. Therefore, HSPDE10A appears to be downregulated in prostate cancer, specifically in adenofibromatous hyperplasia. In the treatment of this and other disorders associated with decreased HSPDE10A expression or activity, it is desirable to increase the expression or activity of HSPDE10A by delivery of the protein, a vector expressing the protein or an agonist of HSPDE10A. In those disorders in which the increased expression of the protein is implicated in the cancerous or immune disease process, it is desirable to decrease expression or activity of HSPDE10A by delivery of an antibody, antagonist, or inhibitor.

Therefore, in one embodiment, HSPDE10A or a fragment or derivative thereof may be administered to a subject to treat a disorder associated with decreased expression or activity of HSPDE10A. Examples of such disorders include, but are not limited to, a cancer, such as cancer such as adenocarcinoma, melanoma, myeloma, sarcoma, and teratocarcinoma of the bone, bone marrow, ganglia, gastrointestinal tract, heart, kidney, liver, lung, muscle, nerve, prostate, testis, and uterus and an immune disorder such as adult respiratory distress syndrome, asthma, atherosclerosis, cholecystitis, Crohn's disease, dermatomyositis, emphysema, erythema nodosum, gastritis, glomerulonephritis, multiple sclerosis, myasthenia gravis, myopathies, osteoarthritis, osteoporosis, polymyositis, rheumatoid arthritis, scleroderma, systemic lupus erythematosus, systemic sclerosis, and ulcerative colitis.

In a second embodiment, a vector capable of expressing HSPDE10A or a fragment or derivative thereof may be administered to a subject to treat a disorder associated with decreased expression or activity of HSPDE10A including, but not limited to, those described above.

In a third embodiment, a composition comprising a substantially purified HSPDE10A in conjunction with a carrier may be administered to a subject to treat a disorder associated with decreased expression or activity of HSPDE10A including, but not limited to, those provided above.

In a fourth embodiment, a composition comprising an agonist which specifically binds HSPDE10A and which increases the expression, activity, or lifespan of HSPDE10A may be administered to a subject to treat a disorder associated with decreased expression or activity of HSPDE10A including, but not limited to, those listed above.

In a fifth embodiment, an antagonist of HSPDE10A may be administered to a subject to treat or prevent a disorder associated with increased expression or activity of HSPDE10A. Such disorders may include, but are not limited to, those discussed above. In one aspect, an antibody which specifically binds HSPDE10A may be used directly as an antagonist or indirectly as a targeting or delivery mechanism for bringing a pharmaceutical agent to cells or tissue which express HSPDE10A.

In a sixth embodiment, a vector expressing the complement of the polynucleotide encoding HSPDE10A may be administered to a subject to treat a disorder associated with increased expression or activity of HSPDE10A including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment of the various disorders described above. Using this approach, one may be able to achieve therapeutic efficacy with lower dosages of each agent, thus reducing the potential for adverse side effects.

An antagonist of HSPDE10A may be produced using methods which are generally known in the art. In particular, purified HSPDE10A may be used to produce antibodies or to screen libraries of pharmaceutical agents to identify those which specifically bind HSPDE10A. Antibodies to HSPDE10A may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies are especially preferred for therapeutic use.

For the production of antibodies, various hosts including goats, rabbits, rats, mice, humans, and others may be immunized by injection with HSPDE10A or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that oligopeptides having from about 5 to about 15 amino acids and selected from the antigenic regions of SEQ ID NOs:1 and 3 are used to induce antibodies to the proteins. These oligopeptides which are identical to epitopes of the natural protein may be fused with those of another protein, such as KLH, and antibodies produced to the chimeric molecule.

Monoclonal antibodies to HSPDE10A may be prepared using any technique which provides for the production of antibody molecules by continuous cell lines in culture. These include, but are not limited to, the hybridoma technique, the human B-cell hybridoma technique, and the EBV-hybridoma technique (Kohler et al. (1975) Nature 256:495–497; Kozbor et al. (1985) J Immunol Methods 81:31–42; Cote et al. (1983) Proc Natl Acad Sci 80:2026–2030; and Cole et al. (1984) Mol Cell Biol 62:109–120).

In addition, techniques developed for the production of "chimeric antibodies," such as the splicing of mouse antibody genes to human antibody genes to obtain a molecule with appropriate antigen specificity and biological activity, can be used (Morrison et al. (1984) Proc Natl Acad Sci 81:6851–6855; Neuberger et al. (1984) Nature 312:604–608; and Takeda et al. (1985) Nature 314:452–454). Alternatively, techniques described for the production of single chain antibodies may be adapted, using methods known in the art, to produce HSPDE10A-specific single chain antibodies. Antibodies with related specificity, but of distinct idiotypic composition, may be generated by chain shuffling from random combinatorial immunoglobulin libraries (Burton (1991) Proc Natl Acad Sci 88:10134–10137).

Antibodies may also be produced by inducing in vivo production in the lymphocyte population or by screening immunoglobulin libraries or panels of highly specific binding reagents as disclosed in the literature (Orlandi et al. (1989) Proc Natl Acad Sci 86: 3833–3837; Winter et al. (1991) Nature 349:293–299).

Antibody fragments which contain specific binding sites for HSPDE10A may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 246:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSPDE10A and its specific antibody. A two-site, monoclonal-based immunoassay utilizing monoclonal antibodies reactive to two non-interfering HSPDE10A epitopes is preferred, but a competitive binding assay may also be employed (Pound, supra).

Various methods such as Scatchard analysis in conjunction with radioimmunoassay techniques may be used to assess the affinity of antibodies for HSPDE10A. Affinity is expressed as an association constant, $K_a$, which is defined as the molar concentration of HSPDE10A-antibody complex divided by the molar concentrations of free antigen and free antibody under equilibrium conditions. The $K_a$ determined for a preparation of polyclonal antibodies, which are heterogeneous in their affinities for multiple HSPDE10A epitopes, represents the average affinity, or avidity, of the antibodies for HSPDE10A. The $K_a$ determined for a preparation of monoclonal antibodies, which are monospecific for a particular HSPDE10A epitope, represents a true measure of affinity. High-affinity antibody preparations with $K_a$ ranging from about $10^9$ to $10^{12}$ l/mole are preferred for use in immunoassays in which the HSPDE10A-antibody complex must withstand rigorous manipulations. Low-affinity antibody preparations with $K_a$ ranging from about $10^6$ to $10^7$ l/mole are preferred for use in immunopurification and similar procedures which ultimately require dissociation of HSPDE10A, preferably in active form, from the antibody (Catty (1988) *Antibodies, Volume I: A Practical Approach*, IRL Press, Washington, D.C.; Liddell and Cryer (1991) *A Practical Guide to Monoclonal Antibodies*, John Wiley & Sons, New York, N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of HSPDE10A-antibody complexes. Procedures for evaluating antibody specificity, titer, and avidity, and guidelines for antibody quality and usage in various applications, are generally available. (See, e.g., Catty, supra, and Coligan, supra.)

In another embodiment of the invention, the polynucleotides encoding HSPDE10A, or any fragment or complement thereof, may be used for therapeutic purposes. In one aspect, the complement of the polynucleotide encoding HSPDE10A may be used in situations in which it would be desirable to block the transcription of the mRNA. In particular, cells may be transformed with sequences complementary to polynucleotides encoding HSPDE10A. Thus, complementary molecules or fragments may be used to modulate HSPDE10A activity, or to achieve regulation of gene function. Such technology is now well known in the art, and sense or antisense oligonucleotides or larger fragments can be designed from various locations along the coding or control regions of sequences encoding HSPDE10A.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HSPDE10A. (See, e.g., Sambrook, supra; Ausubel, 1995, supra.)

Genes encoding HSPDE10A can be turned off by transforming a cell or tissue with expression vectors which express high levels of a polynucleotide, or fragment thereof, encoding HSPDE10A. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HSPDE10A. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described by Gee et al. (1994; In: Huber and Carr, *Molecular and Immunologic Approaches*, Futura Publishing, Mt. Kisco, N.Y., pp. 163–177). A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HSPDE10A.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSPDE10A. Such DNA sequences may be incorporated into a wide variety of vectors with RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods described by Goldman et al. (1997) Nature Biotechnol 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such compositions may consist of HSPDE10A, antibodies to HSPDE10A, and mimetics, agonists, antagonists, or inhibitors of HSPDE10A. The compositions may be administered alone or, which may be administered in any. The compositions may be administered to a patient alone, with a stabilizing compound, with a sterile, biocompatible carrier such as saline, buffered saline, dextrose, or water and in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these compositions may comprise excipients and auxiliaries which facilitate processing of the active compounds. Further details on techniques for formulation and administration may be found in the latest edition of *Remington's Pharmaceutical Sciences* (Maack Publishing, Easton, Pa.).

Pharmaceutical compositions for oral administration can be formulated using pharmaceutically acceptable carriers well known in the art in dosages for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Auxiliaries can be added, if desired. Excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethyl-cellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with coatings, such as concentrated sugar solutions, which may also contain gum arabic, talc, polyvinylpyrrolidone, carbopol gel, polyethylene glycol, and/or titanium dioxide, lacquer solutions, and organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in liquids, such as fatty oils, liquid, or liquid polyethylene glycol with or without stabilizers.

Pharmaceutical formulations for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

Pharmaceutical compositions for use in the invention include compositions wherein the determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HSPDE10A or fragments thereof, antibodies of HSPDE10A, and agonists, antagonists or inhibitors of HSPDE10A, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment.

Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or proteins will be specific to particular cells, conditions, locations, etc.

DIAGNOSTICS

In another embodiment, antibodies which specifically bind HSPDE10A may be used for the diagnosis of disorders such as adenofibromatous hyperplasia of the prostate which is characterized by differential expression of HSPDE10A or in assays to monitor patients being treated with HSPDE10A or agonists, antagonists, or inhibitors of HSPDE10A. Antibodies useful for diagnostic purposes may be prepared in the same manner as described above for therapeutics. Diagnostic assays for HSPDE10A include methods which utilize the antibody and a label to detect HSPDE10A in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HSPDE10A, including ELISAs, RIAs and FACS, are known in the art and provide a basis for diagnosing altered or abnormal levels of HSPDE10A expression. Normal or standard values for HSPDE10A expression are established by combining body fluids or cell extracts taken from normal mammalian subjects, preferably human, with antibody to HSPDE10A under conditions for complex formation. The amount of standard complex formation may be quantitated by various methods, preferably by photometric means. Quantities of HSPDE10A expressed in subject, control, and disease samples from biopsied tissues are compared with the standard values. Deviation between standard and subject values establishes the parameters for diagnosing disease.

In another embodiment of the invention, the polynucleotides encoding HSPDE10A may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HSPDE10A may be correlated with disease. The diagnostic assay may be used to determine absence, presence, and excess expression of HSPDE10A, and to monitor regulation of HSPDE10A levels during therapeutic intervention.

In one aspect, hybridization with PCR probes which are capable of detecting polynucleotide sequences, including genomic sequences, encoding HSPDE10A or closely related molecules may be used to identify nucleic acid sequences which encode HSPDE10A. The specificity of the probe, whether it is made from a highly specific region, such as the 5' regulatory region, or from a less specific region, such as a conserved motif, and the stringency of the hybridization or amplification (maximal, high, intermediate, or low), will determine whether the probe identifies only naturally occurring sequences encoding HSPDE10A, allelic variants, or related sequences.

Probes may also be used for the detection of related sequences, and should preferably have at least 50% sequence identity to any of the HSPDE10A encoding sequences. The hybridization probes of the subject invention may be DNA or RNA and may be derived from the sequence of SEQ ID NO:2 or from genomic sequences including promoters, enhancers, and introns of the HSPDE10A gene.

Means for producing specific hybridization probes for DNAs encoding HSPDE10A include the cloning of polynucleotide sequences encoding HSPDE10A or HSPDE10A derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding HSPDE10A may be used for the diagnosis of disorders associated with expression of HSPDE10A. Examples of such disorders include, but are not limited to, adenocarcinoma, melanoma, myeloma, sarcoma, and teratocarcinoma of the bone, bone marrow, ganglia, gastrointestinal tract, heart, kidney, liver, lung, muscle, nerve, prostate, testis, and uterus and an immune disorder such as adult respiratory distress syndrome, asthma, atherosclerosis, cholecystitis, Crohn's disease, dermatomyositis, emphysema, erythema nodosum, gastritis, glomerulonephritis, multiple sclerosis, myasthenia gravis, myopathies, osteoarthritis, osteoporosis, polymyositis, rheumatoid arthritis, scleroderma, systemic lupus erythematosus, systemic sclerosis, and ulcerative colitis. The polynucleotide sequences encoding HSPDE10A may be used in Southern or northern analysis, dot blot, or other membrane-based technologies; in PCR technologies; in dipstick, pin, and multi-well formats; and in microarrays utilizing fluids or tissues from patients to detect altered HSPDE10A expression. Such qualitative or quantitative methods are well known in the art.

In a particular aspect, the nucleotide sequences encoding HSPDE10A may be useful in assays that detect the presence of associated disorders, particularly those mentioned above. The nucleotide sequences encoding HSPDE10A may be labeled by standard methods and added to a fluid or tissue sample from a patient under conditions for the formation of hybridization complexes. After an incubation period, the sample is washed and the signal is quantitated and compared with a standard value. If the amount of signal in the patient sample is significantly altered in comparison to a control sample then the presence of altered levels of nucleotide sequences encoding HSPDE10A in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HSPDE10A, a normal or standard profile for expression is established. This may be accomplished by combining body fluids or cell extracts taken from normal subjects, either animal or human, with a sequence, or a fragment thereof, encoding HSPDE10A, under conditions for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or over-expressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSPDE10A may involve the use of PCR. These oligomers may be chemically synthesized, generated enzymatically, or produced in vitro. Oligomers will preferably contain a fragment of a polynucleotide encoding HSPDE110A, or a fragment of a polynucleotide complementary to the polynucleotide encoding HSPDE10A, and will be employed under optimized conditions for identification of a specific gene or disorder. Oligomers may also be employed under less stringent conditions for detection or quantitation of closely related DNA or RNA sequences.

Methods which may also be used to quantitate the expression of HSPDE10A include radiolabeling or biotinylating nucleotides, coamplification of a control nucleic acid, and interpolating results from standard curves (Melby et al. (1993) J Immunol Methods 159:235–244; Duplaa et al. (1993) Anal Biochem 229–236). The speed of quantitation of multiple samples may be accelerated by running the assay in an multiwell format where the oligomer of interest is presented in various dilutions and a spectrophotometric or colorimetric response gives rapid quantitation.

In further embodiments, oligonucleotides or longer fragments derived from any of the polynucleotide sequences described herein may be used on a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan et al. (1995) U.S. Pat. No. 5,474,796; Schena et al. (1996) Proc Natl Acad Sci 93:10614–10619; Baldeschweiler et al. (1995) PCT application WO95/251116; Shalon et al. (1995) PCT application 095/35505; Heller et al. (1997) Proc Nati Acad Sci 94:2150–2155; and Heller et al. (1997) U.S. Pat. No. 5,605, 662.)

In another embodiment of the invention, nucleic acid sequences encoding HSPDE10A may be used to generate hybridization probes useful in mapping the naturally occurring genomic sequence. The sequences may be mapped to a particular chromosome, to a specific region of a chromosome, or to artificial chromosome constructions, e.g., HACs, yeast artificial chromosomes (YACs), bacterial artificial chromosomes (BACs), bacterial P1 constructions, or single chromosome cDNA libraries (Harrington, supra; Price (1993) Blood Rev 7:127–134; and Trask (1991) Trends Genet 7:149–154).

Fluorescent in situ hybridization (FISH) may be correlated with other physical chromosome mapping techniques and genetic map data (Heinz-Ulrich et al. (1995) In: Meyers, supra, pp.965–968). Examples of genetic map data can be found in various scientific journals or at the Online Mendelian Inheritance in Man (OMIM) site. Correlation between the location of the gene encoding HSPDE10A on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation (Gatti et al. (1988) Nature 336:577–580). The nucleotide sequence of the subject invention may also be used to detect differences in the chromosomal location due to translocation, inversion, deletion and the like among normal, carrier, or affected individuals.

In another embodiment of the invention, HSPDE10A, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HSPDE10A and the agent being tested may be measured.

Another technique for drug screening provides for high throughput screening of compounds having binding affinity to the protein of interest. (See, e.g., Geysen et al. (1984) PCT application WO84/03564.) In this method, large numbers of different small test compounds are synthesized on a solid substrate. The test compounds are reacted with HSPDE10A, or fragments thereof, and washed. Bound HSPDE10A is then detected by methods well known in the art. Purified HSPDE10A can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSPDE10A specifically compete with a test compound for binding HSPDE10A. In this manner, antibodies can be used to detect the presence of any peptide which shares one or more antigenic determinants with HSPDE10A.

In additional embodiments, the nucleotide sequences which encode HSPDE10A may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The PROSNOT06 cDNA library was constructed from microscopically normal prostate tissue obtained from a 57-year-old Caucasian male. Pathology for the associated tumor indicated adenocarcinoma (Gleason grade 3+3) in both the left and right periphery of the prostrate. Perineural invasion was present as was involvement of periprostatic tissue. Patient history included a benign neoplasm of the large bowel, appendectomy, and tonsillectomy with adenoidectomy. Family history included a malignant neoplasm of the prostate and type I diabetes.

The frozen tissue was homogenized and lysed using a POLYTRON homogenizer (PT-3000; Brinkmann Instruments, Westbury, N.J.) in guanidinium isothiocyanate solution. The lysate was extracted once with acid phenol per Stratagene's RNA isolation protocol (Stratagene, San Diego, Calif.). The RNA was extracted a second time with acid phenol, pH 4.7, precipitated using 0.3 M sodium acetate and 2.5 volumes of ethanol, resuspended in DEPC-treated water, and treated with DNAse at 37° C. for 25 minutes. mRNA was isolated with the OLIGOTEX kit (QIAGEN, Chatsworth, Calif.) and used to construct the cDNA libraries. cDNAs were fractionated on a SEPHAROSE CL4B column (APB), and those cDNAs exceeding 400 bp were ligated into PSPORT1 plasmid (Life Technologies). The plasmid was transformed into DH5α competent cells (Life Technologies).

II Isolation of cDNA Clones

Plasmid DNA was released from the cells and purified using the REAL PREP 96 plasmid kit (QIAGEN). The recommended protocol was employed except for the following changes: 1) the bacteria were cultured in 1 ml of sterile TERRIFIC BROTH (BD Biosciences, Sparks Md.) with carbenicillin at 25 mg/l and glycerol at 0.4%; 2) after inoculation, the cultures were incubated for 19 hours, and the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

III Sequencing and Analysis

The cDNAs were prepared for sequencing using the ABI CATALYST 800 thermal cycler (PE Biosystems), or the HYDRA microdispenser (Robbins Scientific) or the MICROLAB 2200 (Hamilton) systems in combination with the DNA ENGINE thermal cyclers (MJ Research). The cDNAs were sequenced using the ABI PRISM 373 or 377 sequencing systems and standard ABI protocols, base calling software, and kits (PE Biosystems) or using the MEGABACE 1000 DNA sequencing system (APB) with solutions and dyes from APB. Reading frames were determined using standard methods as reviewed in Ausubel (1997, supra, unit 7.7). Some of the cDNA sequences were extended using the techniques disclosed in Example V.

The polynucleotide sequences derived from cDNA, extension, and shotgun sequencing were assembled and analyzed using a combination of software programs which utilize algorithms well known to those skilled in the art.

Table 2 summarizes the software programs, descriptions, references, and threshold parameters used. The first column of Table 2 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering) and LASER-GENE software (DNASTAR).

The polynucleotide sequences were validated by removing vector, linker, and polyA sequences and by masking ambiguous bases, using algorithms and programs based on BLAST, dynamic programming, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, PFAM, and Prosite.

The programs described above for the assembly and analysis of full length polynucleotide and amino acid sequences were used to identify polynucleotide sequence fragments from SEQ ID NO:2. Fragments from about 20 to about 4000 nucleotides which are useful in hybridization and amplification technologies were described in The Invention section above.

IV Cloning of Full Length HSPDE10A

The complete cDNA insert from Incyte clone 826776 was isolated as a Sal1/Not1 restriction fragment, labeled with [α-$^{32}$P]dCTP, and used as a hybridization probe to screen ~1×10$^6$ plaque forming units from a human skeletal muscle 5'-STRETCH PLUS λgt10 cDNA library (Clontech, Cat. #HL5002a). Each cDNA insert was recovered as an EcoRI restriction fragment(s) and subcloned into PBLUESCRIPT KS+ (Stratagene). One λ clone (clone 1a.1) contained a 3.9 kb cDNA insert. Identification of a single, large open reading frame (FIGS. 1A–1E) allowed sequencing of both strands to produce the consensus nucleotide sequence, SEQ ID NO:2. HSPDE10A2, a C-terminal splice variant of HSPDE10A2 was also isolated by hybridization screening of the λ Clontech human skeletal muscle cDNA library. When the clone was isolated and fully sequenced, it revealed an insert with a 5' coding region similar to HSPDE10A1 and a 3' end similar to that of the original Incyte clone 826776 (FIGS. 2A–2F).

V Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Membrane-based northern analysis was performed on RNA samples from a variety of human tissues using Multiple Tissue Northern Blots (Clontech). For detecting human HSPDE10A, the ~1 kb cDNA insert of Incyte clone 826776 (Sal1/Not1 restriction fragment) was used. This comprises 108 bp 5' of the catalytic domain and 429 bp of the catalytic domain that is common to both HSPDE10A1 and HSPDE10A2. To examine HSPDE10A 1 specifically, the ~1.7 kb EcoRI restriction fragment of λ clone 1a.1 which comprises 447 bp of the 3' portion of the catalytic domain and ~1.2 kb of the 3' untranslated region was used.

Each probe was labeled with [α-$^{32}$P]dCTP using a MEGAPRIME kit (Amersham, Buckinghamshire UK) and reaction products (probe) were purified using CHROMASPIN-30 columns (Clontech). The Multiple Tissue Northern blots were pre-hybridized in EXPRESSHYB (Clontech) at 68° C. for 1 hour and hybridized (~1×10$^6$ cpm probe/ml) at 68° C. overnight. Blots were washed in 2×SSPE, 0.05% (w/v) SDS at 50° C. (4×15 mins) followed by 0.1×SSPE, 0.1% (w/v) SDS at 50° C. for 1 hour, and then for 2–7 days. Blots were checked for equal loading of poly(A)$^+$ RNA in each lane using a human β-actin cDNA probe (data not shown).

Northern analysis showed that HSPDE10A was expressed in skeletal muscle and prostate as a major transcript of ~7.5 kb; a ~3.0 kb mRNA was detected only in prostate; and a less prominent transcript of ~1.5 kb occurred in testes and skeletal muscle (FIGS. 5A and 5B). These data suggest that at least three PDE10A splice variants exist. Electronic northern analysis confirms expression in prostate (FIG. 7).

Analogous computer techniques applying BLAST were used to search for identical or related molecules in nucleotide databases such as GenBank or LIFESEQ database (Incyte Genomics). This analysis is much faster than multiple membrane-based hybridizations. In addition, the sensitivity of the computer search is modified to determine whether any particular match is categorized as exact or similar. The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores identify related molecules.

The results of northern analyses were reported as a percentage distribution of libraries in which the transcript encoding HSPDE10A occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, fetal, neurological, and pooled. For each category, the number of libraries expressing the sequence of interest was counted and divided by the total number of libraries across all categories. Percentage values of tissue-specific and disease expression are reported in the description of the invention.

VI Labeling and Use of Individual Hybridization Probes

Hybridization probes derived from SEQ ID NO:2 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250µCi of [$^{32}$P]-adenosine triphosphate (APB), and T4 polynucleotide kinase (NEN Life Science Products, Boston, Mass.). The labeled ligonucleotides are substantially purified using a SEPHADEX G-25 superfine size exclusion dextran bead column (APB). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (NEN Life Science Products).

The DNA from each digest is fractionated on a 0.7% agarose gel and transferred to a NYTRAN PLUS membranes (Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT-AR film (Eastman Kodak, Rochester, N.Y.) is exposed to the blots to film for several hours, hybridization patterns are compared visually.

VII Microarrays

A chemical coupling procedure and an ink jet device is used to synthesize array elements on the surface of a substrate (Baldeschweiler, supra). An array analogous to a dot or slot blot is used to arrange and link elements to the surface of a substrate using thermal, UV, chemical, or mechanical bonding procedures. A typical array is produced by hand or using available methods and machines and contains any appropriate number of elements. After hybridization, nonhybridized probes are removed and a scanner used to determine the levels and patterns of fluorescence. The degree of complementarity and the relative abundance of each probe which hybridizes to an element on the microarray is assessed through analysis of the scanned images.

Full-length cDNAs, expressed sequence tags (ESTs), or fragments thereof comprise the elements of the microarray. Fragments for hybridization are selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using UV cross-linking followed by thermal and chemical treatments and dried (Schena et al. (1995) Science 270:467–470; Shalon et al. (1996) Genome Res 6:639–645). Fluorescent probes are prepared and used for hybridization to the elements on the substrate. The substrate is analyzed by procedures described above.

VIII Complementary Polynucleotides

Sequences complementary to the HSPDE10A-encoding sequences are used to detect, decrease, or inhibit expression of naturally occurring HSPDE10A. Although use of oligonucleotides comprising from about 15 to 30 base pairs is described, essentially the same procedure is used with smaller (PNA) or with larger fragments. Appropriate oligonucleotides are designed using OLIGO 4.06 software (National Biosciences) and the coding sequence of HSPDE10A. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSPDE10A-encoding transcript.

IX Subcloning and Expression of HSPDE10A

Two constructs encoding full length human HSPDE10A1 enzyme (plus and minus an N-terminal epitope tag) were generated for expression in insect cells using a baculovirus vector. Full length human HSPDE10A1 was isolated by PCR from λ clone 1a.1 using a sense primer, 5'-CCAAATCCCGGTCCGAGATGTCCCCAAAGTGCA-GTGCTGATGC-3' (SEQ ID NO:6), covering the initiation codon (underlined) and incorporating an RsrII restriction enzyme site, and an antisense primer, 5'-CGGGTACCTCGAGTTATTAGTTCCTGTCTTCCTT-GGCTACC-3' (SEQ ID NO:7), covering the termination codon (underlined) and incorporating a tandem stop codon and unique XhoI restriction site. PCR was performed using the Expand High Fidelity PCR system (Boehringer Mannheim, West Sussex UK) and the following cycle conditions: 94° C./1'45", 1 cycle; 94° C./15", 65° C./30", 72° C./1'45", 20 cycles, and 72° C./5', 1 cycle. The PCR product was digested with RsrII/XhoI and the resulting restriction fragment ligated into the RsrII/XhoI sites of both the baculovirus transfer vector, pFASTBAC (Life Technologies), and with and without modification to include a 5' FLAG epitope tag (Kunz et al. (1992) J Biol Chem 267:9101–9106). The sequence of the insert for each construct was determined on both strands to confirm identity to the native HSPDE10A1 coding sequence, the encoded sequence being either native HSPDE10A1 or N-terminally FLAG-tagged HSPDE10A1.

Recombinant viral stocks were prepared using the Bacto-Bac system (Life Technologies) according to the manufacturer's protocol, and Sf9 cells were cultured in Sf 900 II serum-free media (Life Technologies) at 27° C. For expression, $3 \times 10^7$ cells in 30 ml were infected at a multiplicity of infection of 1. Cells were harvested 48 hours post-infection for assay. HSPDE10A for enzyme activity assays was prepared from transformed Sf9 cells harvested and disrupted by sonication. Cellular debris was removed by centrifugation at 12,000×g for 15 mins followed by filtration (0.2 µm filter), and the clarified supernatant dialyzed against 20 mM HEPES pH 7.4, 1 mM EDTA, 150 mM NaCl at 4° C. overnight.

HSPDE10A1 was partially purified from the dialyzed supernatant by ion exchange chromatography using a 1 ml Mono Q HR (5/5) column (APB). The column was eluted using a linear NaCl gradient up to 1M, and fractions containing high activity (>70% substrate turnover) were pooled and stored in aliquots at −70° C.

X PAGE and Western Analysis of HSPDE10A

Transformed Sf9 cells were harvested by centrifugation (3,000×g for 10 min), resuspended in homogenization buffer (20 mM HEPES pH 7.2, 1 mM EDTA, 20 mM sucrose, 150 mM NaCl and containing one protease inhibitor tablet (Boehringer Mannheim) per 50 ml) at $1 \times 10^7$ cells/ml and disrupted by sonication. Cellular debris was removed by centrifugation at 12,000×g for 15 min, and the supernatant stored in aliquots at −70° C.

Human PDE10A1 infected and mock infected (control) cell lysates (~$6.4 \times 10^4$ cell equivalents for Coomassie staining, and ~640 cell equivalents for western analysis) were separated by denaturing PAGE using the NuPAGE mini-gel system (Novex, San Diego, Calif.) and either stained with Coomassie or transferred to a polyvinylidene difluoride membrane (Novex) for immunoblotting. Western analysis was performed by enhanced chemiluminescence (APB), according to the manufacturer's protocol using an anti-FLAG antibody (Sigma-Aldrich, Dorset UK) and a horse radish peroxidase conjugated anti-mouse IgG (Bio-Rad, Herts UK) as a secondary antibody at 1:500 and 1:1,000 dilutions, respectively.

XI Demonstration of HSPDE10A Activity

PDE activity of HSPDE10A1 was measured using a scintillation proximity assay (SPA)-based method employing the modification reported by Hurwitz et al. (1984; J Biol Chem 259:8612–8618). 50 μl of 20 mM Tris-HCl pH 7.4 and 5 mM $MgCl_2$ containing the required concentration of cyclic nucleotide was added to 50 μl of diluted enzyme (or no enzyme for background control) in 20 mM Tris-HCl pH 7.4, 5 mM $MgCl_2$ and 2 mg/ml bovine serum albumin to initiate the reaction. Both cAMP and cGMP were used as substrates (0.15–10 μM final concentration) with a 3:1 ratio of unlabeled to [$^3$H]-labeled cAMP or cGMP (APB). Reactions were performed in triplicate in MICROFLUOR plates (Dynex Technologies, Chantilly, Va.) at 30° C. for a period of time that would give less than 25% substrate turnover to avoid non-linearity associated with product inhibition. The reaction was terminated by the addition of 50 μl of PDE SPA beads (yttrium silicate, 20 mg/ml in water; APB) along with a large excess (1 mM final concentration) of the respective unlabeled cyclic nucleotide (cGMP or cAMP). Plates were sealed and shaken for 10 minutes to allow the beads to bind the nucleotide product. The SPA beads were allowed to settle for 30 minutes, and the plates were read on a TOPCOUNT plate reader (Packard Instrument, Meriden, Conn.).

To determine the $K_m$ and $V_{max}$ of the enzyme, the rate of hydrolysis of cAMP and cGMP was measured at a variety of substrate concentrations (0.15–10 μM) using a fixed amount of diluted enzyme over a time-course of 5–60 minutes. Data points in the linear part of the reaction were used to calculate $K_m$ and $V_{max}$ from a Michaelis-Menten plot using the 'Fit Curve' program of EXCEL software (Microsoft, Redmond Wash.).

Inhibition studies were performed using the assay described above except that the appropriate inhibitor, dissolved and diluted as required in dimethylsulphoxide, was added to the diluted enzyme to give the required final concentration (1–200 μM). Reactions were initiated by the addition of substrate. Cyclic GMP was used as substrate at a final concentration of 0.17 μM, a concentration equal to ⅓ $K_m$ so that $IC_{50}$~Ki. Sufficient enzyme was added to give ~25% substrate turnover during a 30 minute incubation at 30° C.

XII Functional Assays

HSPDE10A function is assessed by expressing the sequences encoding HSPDE10A at physiologically elevated levels in mammalian cell culture systems. cDNA is subcloned into pCMV SPORT (Life Technologies) which contains the cytomegalovirus promoter. 5–10 μg of recombinant vector 1–2 μg of an additional plasmid containing CD64-GFP fusion protein (Clontech) are transiently transformed into a human cell line, preferably of endothelial or hematopoietic origin, using either liposome formulations or electroporation. Flow cytometry (FCM) is used to identify transformed cells expressing CD64-GFP. Transformed cells are collected by contacting the cells with CD64-GFP expressed on their surface with magnetic beads coated with either human IgG (DYNAL, Lake Success, N.Y.). mRNA is purified from the cells using methods secribed above and expression of mRNA encoding HSPDE10A is analyzed and quantified by either northern analysis or microarray techniques.

XIII Production of HSPDE10A Specific Antibodies

HSPDE10A purified using PAGE (Harrington (1990) Methods Enzymol 182:488–495), is used to immunize rabbits and to produce antibodies. Alternatively, the HSPDE10A amino acid sequence is analyzed using LASERGENE software (DNASTAR) to determine regions of high immunogenicity, and an oligopeptide is synthesized and used to raise antibodies.

Typically, oligopeptides 15 residues in length are synthesized using an ABI 431A peptide synthesizer (PE Biosystems) using Fmoc-chemistry and coupled to KLH (Sigma-Aldrich, St. Louis, Mo.) by reaction with N-maleimidobenzoyl-N-hydroxysuccinimide ester to increase immunogenicity (Ausubel (1995) supra). Rabbits are immunized with the oligopeptide-KLH complex in complete Freund's adjuvant. Resulting antisera are tested for antipeptide activity by binding the peptide to plastic, blocking with 1% BSA, reacting with rabbit antisera, washing, and reacting with radio-iodinated goat anti-rabbit IgG.

XIV Purification of Naturally Occurring HSPDE10A Using Specific Antibodies

Naturally occurring or recombinant HSPDE10A is substantially purified by immunoaffinity chromatography using antibodies specific for HSPDE10A. An immunoaffinity column is constructed by covalently coupling anti-HSPDE10A antibody to CNBr-activated SEPHAROSE resin (APB). After the coupling, the resin is blocked and washed according to the manufacturer's instructions.

Media containing HSPDE10A are passed over the immunoaffinity column, and the column is washed under high ionic strength buffers in the presence of detergent which allow the preferential absorbance of HSPDE10A. The column is eluted using a buffer of pH 2 to pH 3 or a high concentration of a chaotrope, urea or thiocyanate ion, which disrupts antibody/HSPDE10A binding; and HSPDE10A is collected.

XV Identification of Molecules Which Interact with HSPDE10A

HSPDE10A, or biologically active fragments thereof, are labeled with 1251 Bolton-Hunter reagent (Bolton et al. (1973) Biochem J 133:529–539). Candidate molecules previously arrayed in the wells of a multi-well plate are incubated with the labeled HSPDE10A, washed, and any wells with labeled HSPDE10A complex are assayed. Data obtained using different concentrations of HSPDE10A are used to calculate values for the number, affinity, and association of HSPDE10A with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Inhibitor | Selective for PDE type (IC50) | IC50 for HSPDE10A1 (μM) |
| --- | --- | --- |
| IBMX | non-selective (2–50 μM) | 40 |
| Zaprinast | PDE5/6 (0.8/0.2 μM) | 8 |
| Milrinone | PDE3 (1 μM) | >200 |
| Rolipram | PDE4 (2.0 μM) | 160 |

TABLE 2

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/ PARCEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI Auto-Assembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nuclec Acids Res. 25:3389–3402. | ESTs: Probability value = 1.0E-8 or less Full Length sequences: Probability value = 1.0E-10 or less |
| FASTA | A Pearson and Lipman algorithm that searches for similarity between a query sequence and a group of sequences of the same type. FASTA comprises as least five functions: fasta, tfasta, fastx, tfastx, and ssearch | Pearson, W. R. and D. J. Lipman (1988) Proc. Natl. Acad Sci. 85:2444–2448; Pearson, W. R. (1990) Methods Enzymol. 183:63–98; and Smith, T. F. and M. S. Waterman (1981) Adv. Appl. Math. 2:482–489. | ESTs: fasta E value = 1.06E-6 Assembled ESTs: fasta Identify = 95% or greater and Match length = 200 bases or greater; fastx E value = 1.0E-8 or less Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19:6565–72, 1991. J. G. Henikoff and S. Henikoff(1996) Methods Enzymol. 266:88–105; and Attwood, T. K. et al. (1997) J. Chem. Inf. Comput. Sci. 37: 417–424. | Score = 1000 or greater; Ratio of Score/Strength = 0.75 or larger; and Probability value = 1.0E-3 or less |
| PFAM | A Hidden Markov Models-based application useful for protein family search. | Krogh, A. et al. (1994) J. Mol. Biol., 235: 1501–1531; Sonnhammer, E. L. L. et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25: 217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12:431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. A purified, recombinantly-produced protein comprising the amino acid sequence of SEQ ID NO:1 or SEQ ID NO:3.

2. A purified variant having at least 90% identity to the amino acid sequence of claim 1.

3. A composition comprising the protein of claim 1 and a pharmaceutical carrier.

4. A method of using a protein to produce and purify polyclonal antibodies, the method comprising:
   a) immunizing an animal with the protein of claim 1 under conditions to elicit an antibody response;
   b) isolating animal antibodies; and
   c) screening the isolated antibodies with the protein to purify antibodies which specifically bind the protein.

5. A method of using a protein to produce monoclonal antibodies, the method comprising:
   a) immunizing an animal with the protein of claim 1 under conditions to elicit an antibody response;
   b) isolating antibody-producing cells from the animal;
   c) fusing the antibody-producing cells with immortalized cells in culture to form monoclonal antibody-producing hybridoma cells;
   d) culturing the hybridoma cells;
   e) isolating monoclonal antibodies from culture; and
   f) screening the isolated antibodies with the protein to identify monoclonal antibodies which specifically bind the protein.

6. A method for using a protein to screen a plurality of molecules or compounds to identify a ligand, the method comprising:
   a) combining the protein of claim 1 with the molecules or compounds under conditions to allow specific binding; and
   b) detecting specific binding, thereby identifying a ligand which specifically binds the protein.

7. The method of claim 6 wherein the molecules or compounds are selected from DNA molecules, RNA molecules, peptide nucleic acid molecules, peptides, proteins, agonists, antagonists, antibodies, inhibitors, drug compounds and pharmaceutical agents.

* * * * *